United States Patent
Lee et al.

(10) Patent No.: US 9,115,161 B2
(45) Date of Patent: Aug. 25, 2015

(54) PROCESS FOR PRODUCING POLYCARBONATES AND A COORDINATION COMPLEX USED THEREFOR

(71) Applicant: SK INNOVATION CO., LTD., Seoul (KR)

(72) Inventors: Bun Yeoul Lee, Gyeonggi-do (KR); S. Sujith, Gyeonggi-do (KR); Eun Kyung Noh, Gyeonggi-do (KR); Jae Ki Min, Gyeonggi-do (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 14/273,773

(22) Filed: May 9, 2014

(65) Prior Publication Data

US 2014/0249323 A1    Sep. 4, 2014

Related U.S. Application Data

(62) Division of application No. 13/435,030, filed on Mar. 30, 2012, now Pat. No. 8,829,156, which is a division of application No. 12/598,657, filed as application No. PCT/KR2008/002453 on Apr. 30, 2008, now Pat. No. 8,163,867.

(30) Foreign Application Priority Data

| May 4, 2007 | (KR) | ......................... 10-2007-0043417 |
| Feb. 20, 2008 | (KR) | ......................... 10-2008-0015454 |

(51) Int. Cl.
| C07F 19/00 | (2006.01) |
| C07F 15/02 | (2006.01) |
| C08G 64/00 | (2006.01) |
| C07F 5/02 | (2006.01) |
| C07F 7/10 | (2006.01) |
| C07F 9/28 | (2006.01) |
(Continued)

(52) U.S. Cl.
CPC .............. *C07F 19/005* (2013.01); *C07F 15/025* (2013.01); *C08G 64/34* (2013.01)

(58) Field of Classification Search
None
See application file for complete search history.

(56) References Cited

U.S. PATENT DOCUMENTS

| 4,952,304 A | 8/1990 | Timms |
| 5,064,802 A | 11/1991 | Stevens et al. |
| 5,208,194 A | 5/1993 | Pitchai et al. |

(Continued)

FOREIGN PATENT DOCUMENTS

| JP | 2003-342287 | 12/2003 |
| KR | 10-2004-0061164 | 7/2004 |

(Continued)

OTHER PUBLICATIONS

D. Moore et al., "Mechanism of the Alternating Copolymerization of Epoxides and $CO_2$ Using Beta-Diiminate Zinc Catalysts: Evidence for a Bimetallic Epoxide Enchainment", *J. Am. Chem. Soc.* 2003, 125, 11911-11924.

(Continued)

*Primary Examiner* — Yun Qian
(74) *Attorney, Agent, or Firm* — Clark & Brody

(57) ABSTRACT

The complex of the present invention containing an onium salt and a central Lewis acidic metal has a high catalytic activity at a high temperature for the copolymerization of an epoxide and carbon dioxide to produce a high molecular weight polycarbonate.

3 Claims, 4 Drawing Sheets

(51) Int. Cl.
  *C07F 15/06* (2006.01)
  *C08G 64/34* (2006.01)

(56) References Cited

U.S. PATENT DOCUMENTS

| | | | |
|---|---|---|---|
| 5,399,734 | A | 3/1995 | King, Jr. et al. |
| 5,943,129 | A | 8/1999 | Hoyt et al. |
| 6,133,402 | A | 10/2000 | Coates et al. |
| 6,548,686 | B2 | 4/2003 | Nabika et al. |
| 6,818,437 | B1 | 11/2004 | Gambini et al. |
| 2003/0219754 | A1 | 11/2003 | Oleksy et al. |
| 2006/0192960 | A1 | 8/2006 | Renes et al. |

FOREIGN PATENT DOCUMENTS

| | | |
|---|---|---|
| WO | 01/55231 | 8/2001 |
| WO | 2004/088291 | 10/2004 |

OTHER PUBLICATIONS

G. Coates et al., "Discrete Metal-Based Catalysts for the Copolymerization of $CO_2$ and Epoxides: Discover, Reactivity, Optimization, and Mechanism", *Angew. Chem. Int. Ed.* 2004, 43, 6618-6639.

R. Paddock et al., "Alternating Copolymerization of CO2 and Propylene Oxide Catalyzed by ColII(salen)/Lewis Base", Macromolecules 2005, 38, 6251-6253.

C. Cohen et al., "Copolymerization of cyclohexene oxide and carbon dioxide using (salen)Co(III) complexes: synthesis and characterization of syndiotactic poly(cyclohexene carbonate)", *Dalton Trans.* 2006, 237-249.

A. Haikarainen et al., "Synthesis and characterization of bulky salen-type complexes of Co, Cu, Fe, Mn and Ni with amphiphilic solubility properties", *J. Chem. Soc., Dalton Trans.* 2001, 991-995.

D. Darensbourg et al., "Role of the Cocatalyst in the Copolymerization of CO2 and Cyclohexene Oxide Utilizing Chromium Salen Complexes", J. Am. Chem. Soc. 2005, 127, 14026-14038.

X. Lu et al., "Design of Highly Active Binary Catalyst Systems for CO2/Epoxide Copolymerization: Polymer Selectivity, Enantioselectivity, and Stereochemistry Control", J. Am. Chem. Soc. 2006, 128, 1664-1674.

C. Baleizao et al., "Vanadyl salen complexes covalently anchored to an imidazolium ion as catalysts for the cyanosilylation of aldehydes in ionic liquids", Tetrahedron Letters 44 (2003) 6813-6816.

R. Kureshy et al., "Dicationic chiral Mn(III) salen complex exchanged in the interlayers of montmorillonite clay: a heterogeneous enantioselective catalyst for epoxidation of nonfunctionalized alkenes", Journal of Catalysis 221 (2004) 234-240.

M. Hobday et al., "N,N'-Ethylenebis(Salicylidenteiminato) Transition Metal Ion Chelates", Coordination Chemistry Reviews, 9 (1972-1973) 311-337.

E. Campbell et al., "Unsymmetrical salen-type ligands: high yield synthesis of salen-type Schiff bases containing two different benzaldehyde moieties", Tetrahedron Letters 42 (2001) 1221-1225.

T. Hansen et al., "A high yielding one-pot method for the preparation of salen ligands" Tetrahedron Letters 46 (2005) 3829-3830.

K. Nakano et al., "Selective Formation of Polycarbonate over Cyclic Carbonate: Copolymerization of Epoxides with Carbon Dioxide Catalyzed by a Cobalt(III) Complex with a Piperidinium End-Capping Arm", *Angew. Chem. 2006*, 118, 7432; *Angew. Chem. Int. Ed. 2006*, 45, 7274-7277.

J. Grebe et al., "N-chlorotriphenylphosphaneimine and its Application as an Educt for the Synthesis of Asymmetric PNP Cations. Crystal Structures of Ph3PHCI and [Ph3PNPEt3]Cl"J. anorg. Allg. Chem. 1999, 625,633-636.

D. Darensbourg et al., "Copolymerization of $CO_2$ and Epoxides Catalyzed by Metal Salen Complexes", *Acc. Chem. Res.* 2004, 37, 836-844.

B. Crane et al., "Towards Fluorescence Anisotropy Detection for Real-Time PCR Assays", Proceedings of the 25th Annual Int'l Conf. of the IEEE EMBS, Cancun, Mexico, Sep. 17-21, 2003, pp. 3060-3063.

Nozaki K. et al., "Selective Formation . . . Piperidinium End-Capping Arm" Angewandte Chemie. International Edition, VCH Verlag, Weinheim, DE Nov. 6, 2006, pp. 7247-7277 XP002565055.

Noh et al., JACS, 2007, 129, 8082-8083, Published on Web Jun. 8, 2007.

Coates et al., "Discrete Metal-Based . . . and Mechanism" Angew. Chem. Int. Ed., 2004, 43, 6618-6639.

PROCESS FOR PRODUCING POLYCARBONATES AND A COORDINATION COMPLEX USED THEREFOR

This application is a Divisional of U.S. Ser. No. 13/435,030 filed on Mar. 30, 2012, which is now U.S. Pat. No. 8,829,156, which is a Divisional of U.S. Ser. No. 12/598,657 filed on Nov. 3, 2009, which is now U.S. Pat. No. 8,163,867, which is a national phase of PCT/KR2008/02453 filed on Apr. 30, 2008, which is published as WO2008/136591 on Nov. 13, 2008.

FIELD OF THE INVENTION

The present invention relates to a process for producing a polycarbonate using an epoxide and carbon dioxide and a novel coordination complex which is useful as a catalyst therefor.

BACKGROUND OF THE INVENTION

Aliphatic polycarbonates are known to be biodegradable and widely used for packages, coatings and others. An aliphatic polycarbonate can be prepared by copolymerizing an epoxide with carbon dioxide, which is environment-friendly since a toxic compound such as phosgene is not used. For such a process, there have been developed various types of catalysts, e.g., metallic zinc compounds.

There have recently been reported highly active binary catalyst systems comprising (Salen)Co or (Salen)Cr derivatives (wherein H$_2$Salen is N,N'-bis(3,5-dialkylsalicylidene)-1,2-cyclohexanediamine) combined with an onium salt such as [R$_4$N]Cl and PPNCl (bis(triphenylphosphine)iminium chloride) or a base such as an amine and phosphine. [(Salen) Co system: (a) Lu, X.-B.; Shi, L.; Wang, Y.-M.; Zhang, R.; Zhang, Y.-J.; Peng, X.-J.; Zhang, Z.-C.; Li, B. *J. Am. Chem. Soc.* 2006, 128, 1664; (b) Cohen, C. T. Thomas, C. M. Peretti, K. L. Lobkovsky, E. B. Coates, G. W. *Dalton Trans.* 2006, 23.; (c) Paddock, R. L. Nguyen, S. T. *Macromolecules* 2005, 38, 6251; (Salen)Cr system: (a) Darensbourg, D. J.; Phelps, A. L.; Gall, N. L.; Jia, L. *Acc. Chem. Res.* 2004, 37, 836; (b) Darensbourg, D. J.; Mackiewicz, R. M. *J. Am. Chem. Soc.* 2005, 127, 14026]

In case of using a binary catalyst system comprising a (Salen)Co compound, the oxygen atom of an epoxide coordinates to the central Co atom having Lewis acid character and carbonate anion generated by the action of an onium salt or bulky amine base reacts with the activated epoxide through nucleophilic attack as shown below. With this system, the polymerization was conducted typically under the conditions that [epoxide]/[catalyst] is 2,000 and temperature is below 45° C., with the maximum turnover number (TON) of 980 and the turnover frequency (TOF) of 1400 h$^{-1}$.

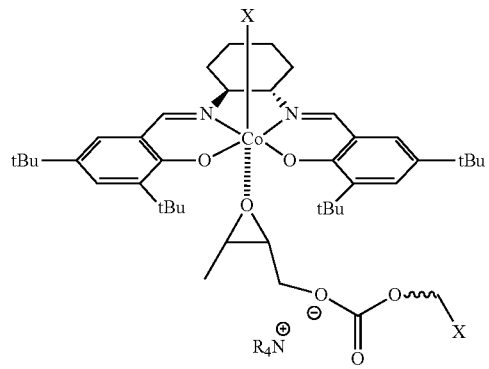

Coates, G. W. et al. have also developed a highly active catalyst composed of a zinc complex having a β-diketiminate ligand, which shows a high turnover rate of 1,116 turnover/hr [Coates, G. W. Moore, D. R. *Angew. Chem., Int. Ed.* 2004, 6618; U.S. Pat. No. 6,133,402]. Coates et al. achieved a still higher turnover rate of 2,300 turnover/hr when a zinc catalyst having a similar structure is used [*J. Am. Chem. Soc.* 125, 11911-11924 (2003)]. The catalytic action of the zinc complex comprising β-diketiminate ligand has been proposed to occur as shown below [Moore, D. R.; Cheng, M.; Lobkovsky, E. B.; Coates, G. W. *J. Am. Chem. Soc.* 2003, 125, 11911].

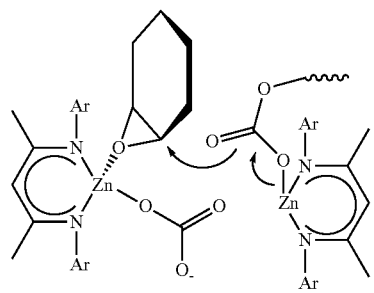

Under above-mentioned mechanisms, the catalystic systems have some drawbacks that will prevent them from being commercially available. It is conceptually difficult to achieve a high turnover number (TON) under these mechanisms. In order to achieve a high TON, the catalyst should therefore be active even at a high [monomer]/[catalyst] ratio condition. However, at this condition, the chance for the chain-growing carbonate unit to meet the coordinated epoxide is diminished, consequently resulting in a low activity. Because all the addition polymerization reaction is exothermic, heat removal during polymerization is a key issue in designing the process. If the catalyst works at a reasonably high temperature, we can remove the heat by using ambient water or air, but if the catalyst works only at a low temperature, for instance, room temperature, we have to use some cryogen, which makes the process expensive. In a solution or bulk polymerization, the attainable conversion of monomer to the polymer is limited by the viscosity caused by formation of polymer. If we can run the polymerization at a higher temperature, we can convert more monomers to polymers because the viscosity is reduced as the temperature is increased. For the propagation mechanism shown above, the $\Delta S^{\ddagger}$ is negative and the activation energy ($\Delta G^{\ddagger}$) for the step increases as the temperature increases, leading to a lower activity at a higher temperature.

The TON and TOF values achieved by a binary catalyst system comprising a (Salen)Co compound or a zinc complex having a β-diketiminate ligand are still low enough to warrant to further improvement, because low activity means higher catalyst cost and higher levels of catalyst-derived metal residue in the resin. This metal residue either colours the resin or causes toxicity. While TON of 980 attained with a binary catalyst system comprising a (Salen)Co compound for CO$_2$/(propylene oxide) copolymerization, the residual cobalt level in the resin reached 600 ppm unless it was removed.

Therefore, there has been a need to develop a catalyst which is capable of polymerizing an acyclic epoxide or a cyclic epoxide at a high rate under a high-temperature industrial condition or at a highly diluted condition, to produce a polymer having a high molecular weight.

Further, there have been made many unsuccessful attempts to recover catalysts from polymer products after polymerization, and, therefore, it is another object of the present invention to provide an effective way to recover active catalysts after use.

SUMMARY OF THE INVENTION

In accordance with one aspect of the present invention, there is provided a process for producing a polycarbonate comprising subjecting an epoxide and carbon dioxide to a copolymerization reaction in the presence of a complex, wherein the complex comprises one central metal atom which serves as a Lewis acid site and at least one functional moiety selected from the group consisting of those represented by formula (1), formula (2) and formula (3):

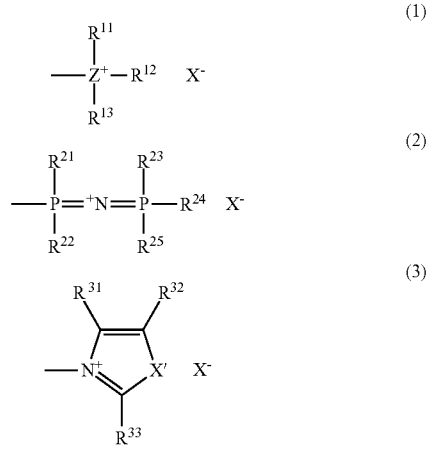

wherein

Z is nitrogen or phosphorus;

X is halogen; $C_6$-$C_{20}$ aryloxy; $C_6$-$C_{20}$ aryloxy having one or more functional moieties selected from the group consisting of halogen, nitrogen, oxygen, silicon, sulfur and phosphorus; $C_1$-$C_{20}$ carboxy; $C_1$-$C_{20}$ carboxy having one or more functional moieties selected from the group consisting of halogen, nitrogen, oxygen, silicon, sulfur and phosphorus; $C_1$-$C_{20}$ alkoxy; $C_1$-$C_{20}$ alkoxy having one or more functional moieties selected from the group consisting of halogen, nitrogen, oxygen, silicon, sulfur and phosphorus; $C_1$-$C_{20}$ alkylsulfonato; $C_1$-$C_{20}$ alkylsulfonato having one or more functional moieties selected from the group consisting of halogen, nitrogen, oxygen, silicon, sulfur and phosphorus; $C_1$-$C_{20}$ amido; or $C_1$-$C_{20}$ amido having one or more functional moieties selected from the group consisting of halogen, nitrogen, oxygen, silicon, sulfur and phosphorus;

$R^{11}$, $R^{12}$, $R^{13}$, $R^{21}$, $R^{22}$, $R^{23}$, $R^{24}$ and $R^{25}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{11}$, $R^{12}$ and $R^{13}$, or two of $R^{21}$, $R^{22}$, $R^{23}$, $R^{24}$ and $R^{25}$ being optionally fused together to form a bridged structure;

$R^{31}$, $R^{32}$ and $R^{33}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus; or a metalloid radical of group XIV metal substituted by hydrocarbyl, two of $R^{31}$, $R^{32}$ and $R^{33}$ being optionally fused together to form a bridged structure;

X' is oxygen, sulfur or N—R;

R is hydrogen; $C_1$-$C_{20}$ alkyl; $C_1$-$C_{20}$ alkyl having one or more functional moieties selected from the group consisting of halogen, nitrogen, oxygen, silicon, sulfur and phosphorus; $C_2$-$C_{20}$ alkenyl; $C_2$-$C_{20}$ alkenyl having one or more functional moieties selected from the group consisting of halogen, nitrogen, oxygen, silicon, sulfur and phosphorus; $C_7$-$C_{20}$ alkylaryl; $C_7$-$C_{20}$ alkylaryl having one or more functional moieties selected from the group consisting of halogen, nitrogen, oxygen, silicon, sulfur and phosphorus; $C_7$-$C_{20}$ arylalkyl; $C_7$-$C_{20}$ arylalkyl having one or more functional moieties selected from the group consisting of halogen, nitrogen, oxygen, silicon, sulfur and phosphorus.

In accordance with another aspect of the present invention, the catalytic complex may be recovered by a process comprising the steps of treating the reaction mixture containing the polycarbonate and the complex with a composite-forming material to form a composite of the complex and the composite-forming material; removing the composite from the reaction mixture; and recovering the complex from the composite by treating the composite in a medium which does not dissolve the composite-forming material with an acid and/or a non-reactive metal salt, and isolating the complex released into the medium.

In accordance with further another aspect of the present invention, there is provided a polycarbonate produced by the above process, wherein the metal content of the polycarbonate is below 15 ppm.

In accordance with further another aspect of the present invention, there is provided a complex of formula (4a):

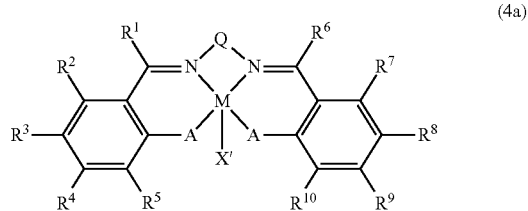

wherein

M is Co or Cr;

X' is each independently halogen; $C_6$-$C_{20}$ aryloxy unsubstituted or substituted by nitro; or $C_1$-$C_{20}$ carboxy unsubstituted or substituted by halogen;

A is oxygen;

Q is trans-1,2-cyclohexylene, ethylene or substituted ethylene;

$R^1$, $R^2$, $R^4$, $R^6$, $R^7$ and $R^9$ are hydrogen;

$R^5$ and $R^{10}$ are each independently hydrogen, tert-butyl, methyl or isopropyl;

one or both of $R^3$ and $R^8$ are —[$YR^{41}_{3-m}\{(CR^{42}R^{43})_n NR^{44}R^{45}R^{46}\}_m]X'_m$ or —[$PR^{51}R^{52}$=N=$PR^{53}R^{54}R^{55}]X'$, the other being hydrogen, methyl, isopropyl or tert-butyl;

Y is C or Si;

$R^{41}$, $R^{42}$, $R^{43}$, $R^{44}$, $R^{45}$, $R^{46}$, $R^{51}$, $R^{52}$, $R^{53}$, $R^{54}$ and $R^{55}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^{44}$, $R^{45}$ and $R^{46}$, or two of $R^{51}$, $R^{52}$, $R^{53}$, $R^{54}$ and $R^{55}$ being optionally fused together to form a bridged structure;

m is an integer in the range of 1 to 3; and n is an integer in the range of 1 to 20.

In accordance with further another aspect of the present invention, there is provided a compound of formula (7a) which may be used for producing a complex of formula (4a):

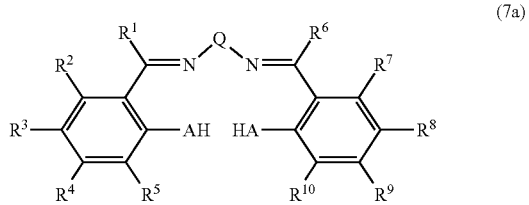

(7a)

wherein

A is oxygen;

Q is trans-1,2-cyclohexylene, ethylene or substituted ethylene;

$R^1$, $R^2$, $R^4$, $R^6$, $R^7$ and $R^9$ are hydrogen;

$R^5$ and $R^{10}$ are each independently hydrogen, tert-butyl, methyl or isopropyl;

one or both of $R^3$ and $R^8$ are —[$YR^{41}_{3-m}\{(CR^{42}R^{43})_n NR^{44}R^{45}R^{46}\}_m]X'_m$ or —[$PR^{51}R^{52}$=N=$PR^{53}R^{54}R^{55}]X'$, and the other is hydrogen, methyl, isopropyl or tert-butyl;

X' is as defined for formula (4a);

Y is C or Si;

$R^{41}$, $R^{42}$, $R^{43}$, $R^{44}$, $R^{45}$, $R^{46}$, $R^{51}$, $R^{52}$, $R^{53}$, $R^{54}$ and $R^{55}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^{44}$, $R^{45}$ and $R^{46}$, or two of $R^{51}$, $R^{52}$, $R^{53}$, $R^{54}$ and $R^{55}$ being optionally fused together to form a bridged structure;

m is an integer in the range of 1 to 3; and n is an integer in the range of 1 to 20.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
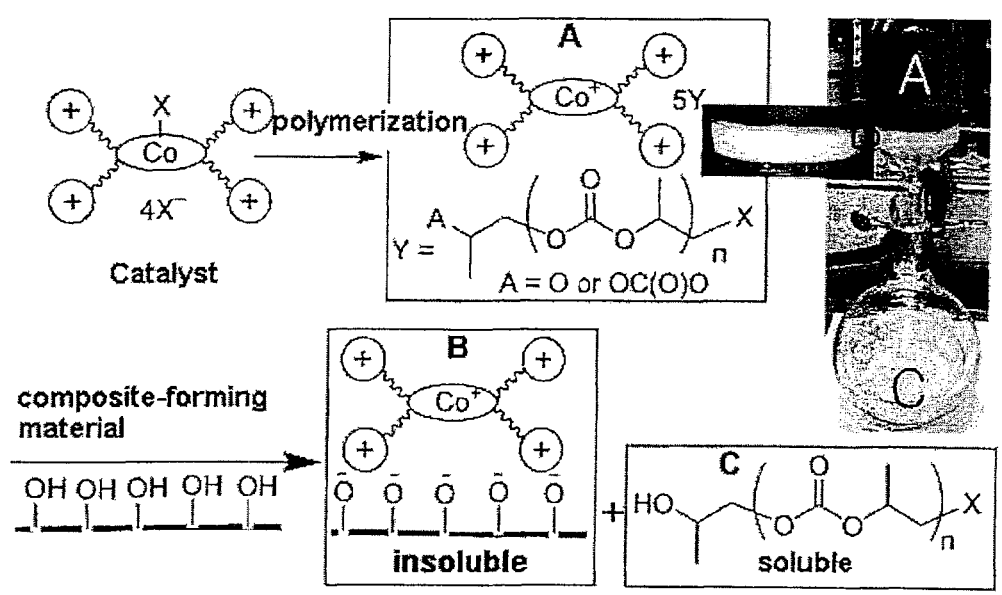
FIG. 1: a schematic diagram of the step of treating the reaction mixture containing the polycarbonate and the complex with a composite-forming material to form a composite of the complex and the composite-forming material.

According to an embodiment of the present invention, a polycarbonate may be produced by copolymerizing an epoxide and carbon dioxide in the presence of a catalytic complex having at least one functional group selected from the group consisting of those represented by (1), formula (2) and formula (3), and a central metal which is a Lewis acid site.

Examples of the epoxide compound which may be used in the copolymerization are selected from the group consisting of $C_2$-$C_{20}$ alkylene oxide unsubstituted or substituted by halogen or alkoxy, $C_4$-$C_{20}$ cycloalkene oxide unsubstituted or substituted by halogen or alkoxy, and $C_8$-$C_{20}$ styrene oxide unsubstituted or substituted by halogen, alkoxy or alkyl.

Particular examples of the epoxide compound may include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrin, epichlorohydrin, epibromohydrin, isopropyl glycidyl ether, butyl glycidyl ether, tert-butyl glycidyl ether, 2-ethylhexyl glycidyl ether, allyl glycidyl ether, cyclopentene oxide, cyclohexene oxide, cyclooctene oxide, cyclododecene oxide, α-pinene oxide, 2,3-epoxynorbornene, limonene oxide, dieldrine, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, etc.

According to another embodiment of the present invention, the polymerization reaction may be conducted in a solvent to obtain a solution of the polycarbonate and the complex.

The organic solvent may include aliphatic hydrocarbon, such as pentane, octane, decane and cyclohexane; aromatic hydrocarbon, such as benzene, toluene and xylene; halogenated hydrocarbon, such as chloromethane, methylene chloride, chloroform, carbon tetrachloride, 1,1-dichloroethane, 1,2-dichloroethane, ethyl chloride, trichloroethane, 1-chloropropane, 2-chloropropane, 1-chlorobutane, 2-chlorobutane, 1-chloro-2-methylpropane, chlorobenzene and bromobenzene, and the combination thereof. Preferably, bulk polymerization is performed, in which the epoxide compound serves as a solvent.

The volume ratio of the solvent to the epoxide compound may be from 0:100 to 99:1, preferably from 0:100 to 90:1.

The molar ratio of the epoxide to the catalyst may be from 1,000:1 to 500,000:1, preferably from 10,000:1 to 100,000:1. At this time, the turnover rate of the catalyst is 500 turnover/hr or more.

The pressure of carbon dioxide may be in the range of from 1 to 100 atm, preferably 2-50 atm. The polymerization temperature may be in the range of from 20 to 120° C., preferably from 50 to 100° C.

The polycarbonate may be produced using a polymerization method, such as batch, semi-batch, or continuous process. In the batch or semi-batch process, the reaction time may be from 1 to 24 hours, preferably from 1.5 to 6 hours. Further, in the continuous process, the mean residence time of the catalyst is preferably from 1 to 24 hours.

According to the method of the present invention, a polycarbonate having a number average molecular weight (Mn) of 5,000 to 1,000,000 and a molecular weight distribution index (Mw/Mn) of 1.05 to 4.0 may be produced. The number average molecular weight (Mn) and the weight average molecular weight (Mw) are measured by gel permeation chromatography (GPC).

The polycarbonate thus produced composed of at least 90% carbonate bond, often at least 99% carbonate bond, and it is easily biodegradable and useful for packaging and coating.

The polymerizing process of the present invention employs a complex containing at least one functional group selected from the group consisting of those represented by (1), formula (2) and formula (3), and a central Lewis acidic metal.

A preferable embodiment of "complexes including a functional group selected from the group consisting of those represented formula (1), formula (2) and formula (3), and a central Lewis acidic metal is represented by formula (4):

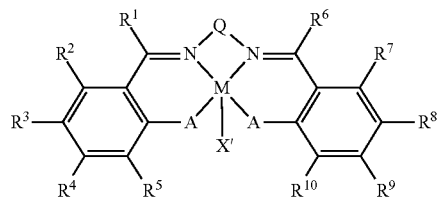

(4)

wherein
M is a metal;
X' is a neutral or a monovalent anion ligand;
A is oxygen or sulfur;
Q is $C_1$-$C_{20}$ alkylene; $C_1$-$C_{20}$ alkylene having one or more functional moieties selected from the group consisting of halogen, nitrogen, oxygen, silicon, sulfur and phosphorous; $C_3$-$C_{20}$ cycloalkyl diradical; $C_3$-$C_{20}$ cycloalkyl diradical having one or more functional moieties selected from the group consisting of halogen, nitrogen, oxygen, silicon, sulfur and phosphorous; $C_6$-$C_{30}$ aryl diradical; $C_6$-$C_{30}$ aryl diradical having one or more functional moieties selected from the group consisting of halogen, nitrogen, oxygen, silicon, sulfur and phosphorous; $C_1$-$C_{20}$ dioxy radical; or $C_1$-$C_{20}$ dioxy radical having one or more functional moieties selected from the group consisting of halogen, nitrogen, oxygen, silicon, sulfur and phosphorous;
$R^1$ to $R^{10}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^1$ to $R^{10}$ being optionally fused together to form a bridged structure; and at least one of $R^1$ to $R^{10}$ is a functional group selected from the group consisting of those represented by formula (1), formula (2) and formula (3).

Although a compound having the functional moiety of formula (1) has been known, e.g., J. Chem. Soc., Dlaton Trans., 2001, 991; Tetrahedron Lett. 2003, 44, 6813; Journal of Catalysis 2004, 221, 234, the use of the compound as a catalyst for polymerization of an epoxide and carbon dioxide has not been suggested.

The more preferred embodiment of the complex according to present invention may be represented by formula (4a)

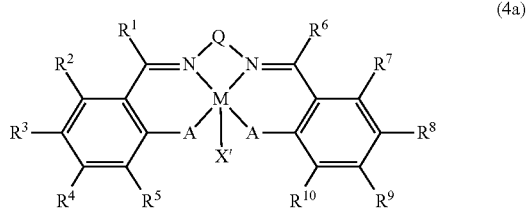

(4a)

wherein
M is Co or Cr;
X' is each independently halogen; $C_6$-$C_{20}$ aryloxy unsubstituted or substituted by nitro; or $C_1$-$C_{20}$ carboxy unsubstituted or substituted by halogen;
A is oxygen;
Q is trans-1,2-cyclohexylene, ethylene or substituted ethylene;
$R^1$, $R^2$, $R^4$, $R^6$, $R^7$ and $R^9$ are hydrogen;
$R^5$ and $R^{10}$ are each independently hydrogen, tert-butyl, methyl or isopropyl; one or both of $R^3$ and $R^8$ are —[Y$R^{41}_{3-m}${(C$R^{42}R^{43}$)$_n$N$R^{44}R^{45}R^{46}$}$_m$]X'm or —[P$R^{51}R^{52}$=N—P$R^{53}R^{54}R^{55}$]X', the other being hydrogen, methyl, isopropyl or tert-butyl;
Y is C or Si;
$R^{41}$, $R^{42}$, $R^{43}$, $R^{44}$, $R^{45}$, $R^{46}$, $R^{51}$, $R^{52}$, $R^{53}$, $R^{54}$ and $R^{55}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^{44}$, $R^{45}$ and $R^{46}$, or two of $R^{51}$, $R^{52}$, $R^{53}$, $R^{54}$ and $R^{55}$ being optionally fused together to form a bridged structure;
m is an integer in the range of 1 to 3; and
n is an integer in the range of 1 to 20.

More specific examples of the complexes according to present invention are represented by formula (5a) to formula (5e):

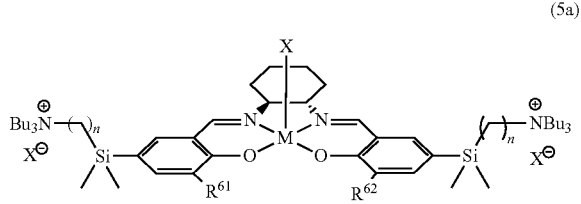
(5a)

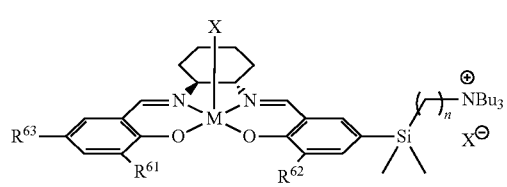
(5b)

-continued

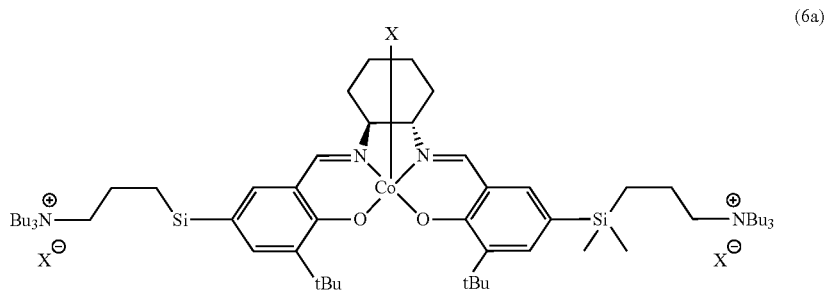
(5c)
(5d)
(5e)

wherein
M is Co or Cr;
$R^{61}$, $R^{62}$ and $R^{63}$ are each independently hydrogen, methyl, isopropyl or tert-butyl;

X is halogen; $C_6$-$C_{20}$ aryloxy; $C_6$-$C_{20}$ aryloxy having one or more functional moieties selected from the group consisting of halogen, nitrogen, oxygen, silicon, sulfur and phosphorous; $C_1$-$C_{20}$ carboxy; $C_1$-$C_{20}$ carboxy having one or more functional moieties selected from the group consisting of halogen, nitrogen, oxygen, silicon, sulfur and phosphorous; $C_1$-$C_{20}$ alkoxy; $C_1$-$C_{20}$ alkoxy having one or more functional moieties selected from the group consisting of halogen, nitrogen, oxygen, silicon, sulfur and phosphorous; $C_1$-$C_{20}$ alkylsulfonato; $C_1$-$C_{20}$ alkylsulfonato having one or more functional moieties selected from the group consisting of halogen, nitrogen, oxygen, silicon, sulfur and phosphorous; $C_1$-$C_{20}$ amido; or $C_1$-$C_{20}$ amido having one or more functional moieties selected from the group consisting of halogen, nitrogen, oxygen, silicon, sulfur and phosphorous; and n is an integer in the range of 1 to 20.

Still more specific examples of the complexes according to present invention are represented by formula (6a) to formula (6f):

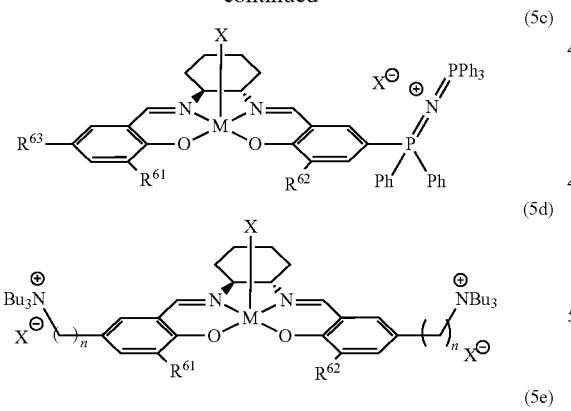
(6a)

wherein X is 2,4-dinitrophenoxy;

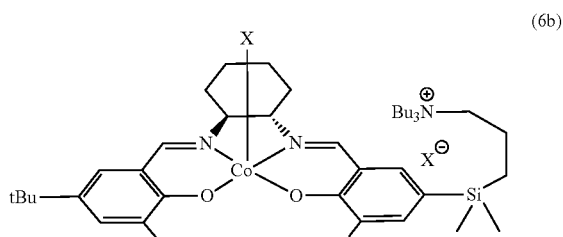
(6b)

wherein X is 2,4-dinitrophenoxy;

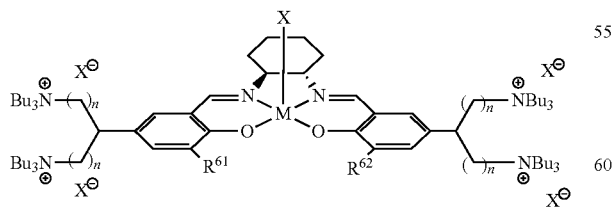
(6c)

wherein X is Cl;

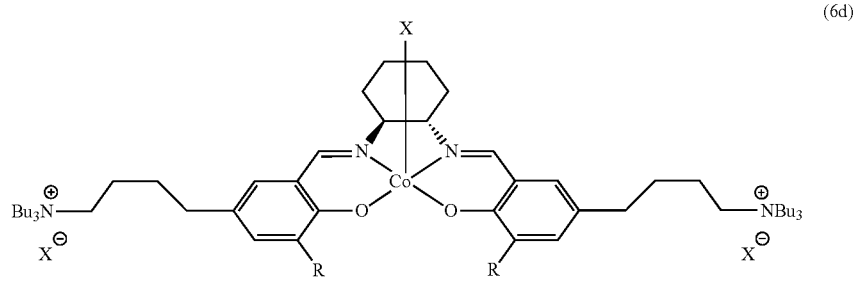

(6d)

wherein X is 2,4-dinitrophenoxy, and R is methyl, isopropyl or tert-butyl;

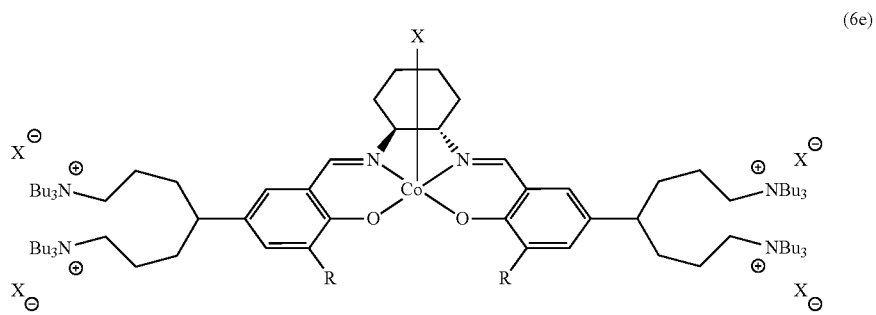

(6e)

wherein X is 2,4-dinitrophenoxy, and R is methyl, isopropyl or tert-butyl;

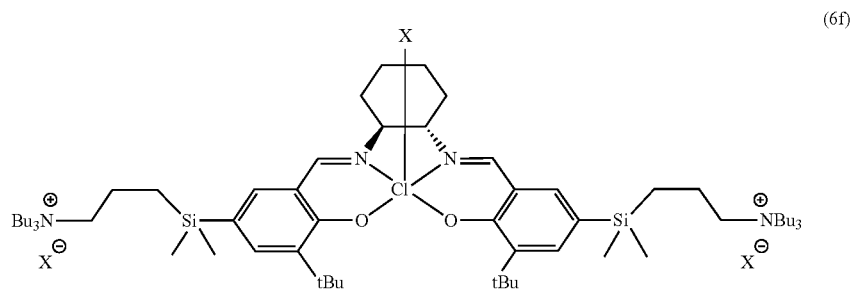

(6f)

wherein X is Cl.

The complexes of formula (4) can be synthesized from the compound of formula (7) using a method similar to those known in the art, e.g., Hobday, M. D.; Smith, T. D.; *Coord. Chem. Rev.* vol. 9, 1972-1973, 311; Cohen, C. T.; Thomas, C. M.; Peretti, K. L.; Lobkovsky, E. B.; Coates, G. W.; *Dalton Trans.* 2006, 237.

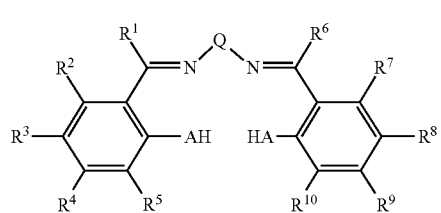

(7)

wherein
A is oxygen or sulfur;
Q is $C_1$-$C_{20}$ alkylene; $C_1$-$C_{20}$ alkylene having one or more functional moieties selected from the group consisting of halogen, nitrogen, oxygen, silicon, sulfur and phosphorous; $C_3$-$C_{20}$ cycloalkyl diradical; $C_3$-$C_{20}$ cycloalkyl diradical having one or more functional moieties selected from the group consisting of halogen, nitrogen, oxygen, silicon, sulfur and phosphorous; $C_6$-$C_{30}$ aryl diradical; $C_6$-$C_{30}$ aryl diradical having one or more functional moieties selected from the group consisting of halogen, nitrogen, oxygen, silicon, sulfur and phosphorous; $C_1$-$C_{20}$ dioxy radical; or $C_1$-$C_{20}$ dioxy radical having one or more functional moieties selected from the group consisting of halogen, nitrogen, oxygen, silicon, sulfur and phosphorous;

$R^1$ to $R^{10}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^1$ to $R^{10}$ being optionally fused together to form a bridged structure; and at least one of $R^1$ to $R^{10}$ is a functional group selected from the group consisting of those represented by formula (1), formula (2) and formula (3).

In case X in the function group of formula (1) or formula (2) interrupts the introduction of a metal, X may be replaced by $BF_4$ anion which is less reactive, and, after the introduction of the metal into the compound, $BF_4$ anion may be replaced by X.

Similarly, the complexes of formula (4a) can be synthesized from the compound of formula (7a):

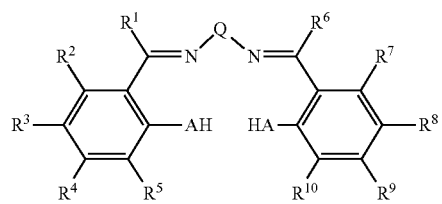

(7a)

wherein

A is oxygen;

Q is trans-1,2-cyclohexylene, ethylene or substituted ethylene;

$R^1$, $R^2$, $R^4$, $R^6$, $R^7$ and $R^9$ are hydrogen;

$R^5$ and $R^{10}$ are each independently hydrogen, tert-butyl, methyl or isopropyl;

one or both of $R^3$ and $R^8$ are $-[YR^{41}_{3-m}\{(CR^{42}R^{43})_n NR^{44}R^{45}R^{46}\}_m]X'_m$ or $-[PR^{51}R^{52}=N=PR^{53}R^{54}R^{55}]X'$, and the other is hydrogen, methyl, isopropyl or tert-butyl;

X' is as defined for formula (4a);

Y is C or Si;

$R^{41}$, $R^{42}$, $R^{43}$, $R^{44}$, $R^{45}$, $R^{46}$, $R^{51}$, $R^{52}$, $R^{53}$, $R^{54}$ and $R^{55}$ are each independently hydrogen; $C_1$-$C_{20}$ alkyl; $C_1$-$C_{20}$ alkyl having one or more functional moieties selected from the group consisting of halogen, nitrogen, oxygen, silicon, sulfur and phosphorous; $C_2$-$C_{20}$ alkenyl; $C_2$-$C_{20}$ alkenyl having one or more functional moieties selected from the group consisting of halogen, nitrogen, oxygen, silicon, sulfur and phosphorous; $C_7$-$C_{20}$ alkylaryl; $C_7$-$C_{20}$ alkylaryl having one or more functional moieties selected from the group consisting of halogen, nitrogen, oxygen, silicon, sulfur and phosphorous; $C_7$-$C_{20}$ arylalkyl; $C_7$-$C_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of $R^{44}$, $R^{45}$ and $R^{46}$, or two of $R^{51}$, $R^{52}$, $R^{53}$, $R^{54}$ and $R^{55}$ being optionally fused together to form a bridged structure;

m is an integer in the range of 1 to 3; and n is an integer in the range of 1 to 20.

Particular examples of the compound of formula (7a) are the compounds of formula (8a) to formula (8e):

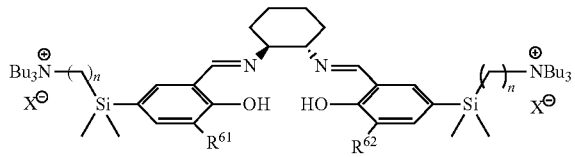

(8a)

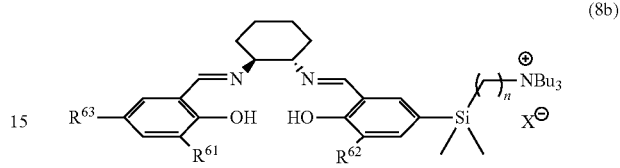

(8b)

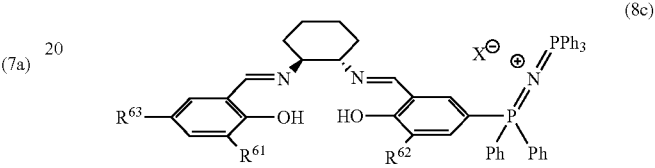

(8c)

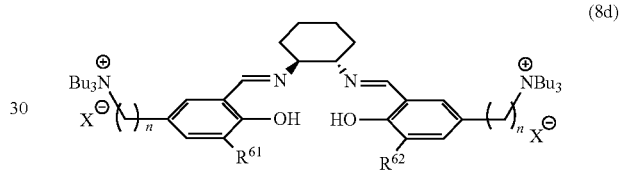

(8d)

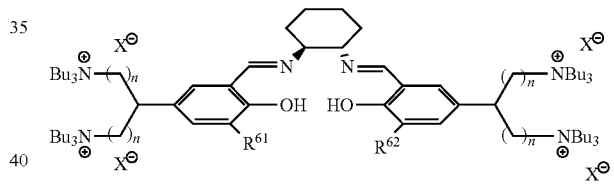

(8e)

wherein $R^{61}$, $R^{62}$ and $R^{63}$ are each independently hydrogen, methyl, isopropyl or tert-butyl;

X is halogen; $BF_4$; $C_6$-$C_{20}$ aryloxy; $C_6$-$C_{20}$ aryloxy having one or more functional moieties selected from the group consisting of halogen, nitrogen, oxygen, silicon, sulfur and phosphorous; $C_1$-$C_{20}$ carboxy; $C_1$-$C_{20}$ carboxy having one or more functional moieties selected from the group consisting of halogen, nitrogen, oxygen, silicon, sulfur and phosphorous; $C_1$-$C_{20}$ alkoxy; $C_1$-$C_{20}$ alkoxy having one or more functional moieties selected from the group consisting of halogen, nitrogen, oxygen, silicon, sulfur and phosphorous; $C_1$-$C_{20}$ alkylsulfonato; $C_1$-$C_{20}$ alkylsulfonato having one or more functional moieties selected from the group consisting of halogen, nitrogen, oxygen, silicon, sulfur and phosphorous; $C_1$-$C_{20}$ amido; or $C_1$-$C_{20}$ amido having one or more functional moieties selected from the group consisting of halogen, nitrogen, oxygen, silicon, sulfur and phosphorous; and n is an integer in the range of 1 to 20.

More particular examples of the compound of formula (7) are the compounds of formula (9a) to formula (9f):

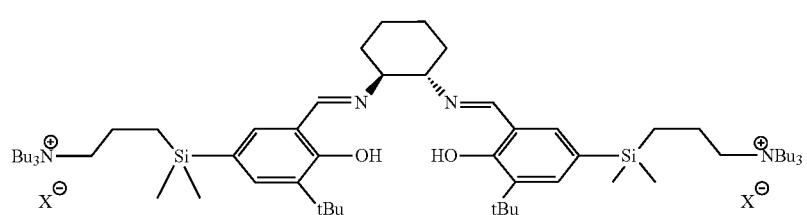
(9a)
wherein X is halogen, BF₄ or 2,4-dinitrophenoxy;
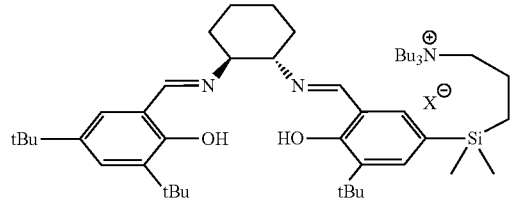
(9b)
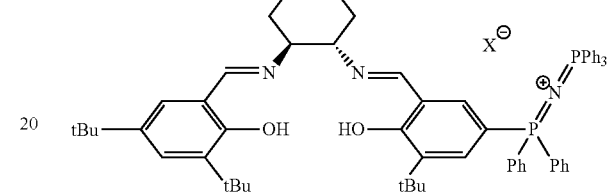
(9c)
wherein X is halogen, BF₄ or 2,4-dinitrophenoxy;
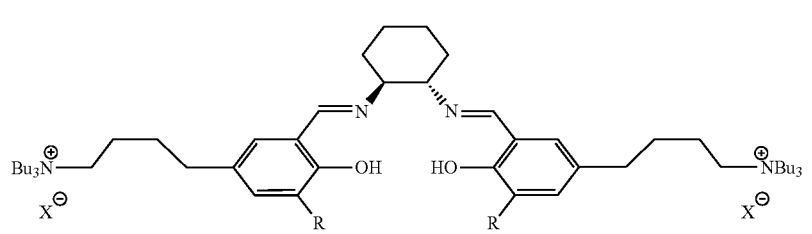
(9d)
wherein X is halogen, BF₄ or 2,4-dinitrophenoxy, and R is methyl, isopropyl or tert-butyl;
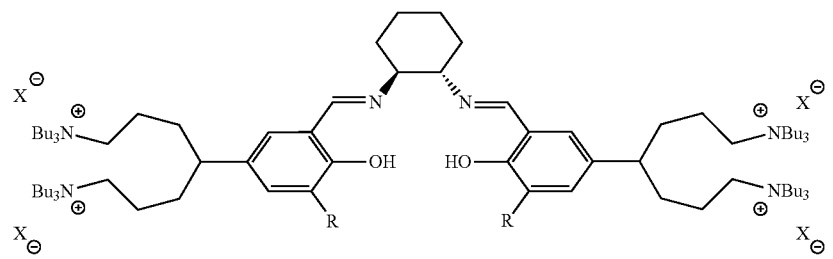
(9e)
wherein X is halogen, BF₄ or 2,4-dinitrophenoxy, and R is methyl, isopropyl or tert-butyl.
;
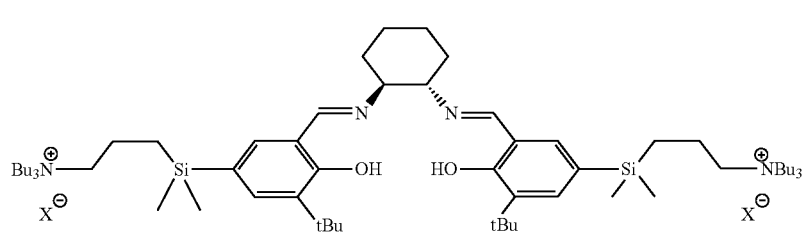
(9f)
wherein X is Cl.

The compounds of formula (7) may be produced by Schiff's base condensation reaction of the compound of formula (10) and $H_2N$-A-$NH_2$ using the known procedure [E. J. Campbell, S. T. Nguyen, *Tetrahedron Lett.* 2001, 42, 1221.].

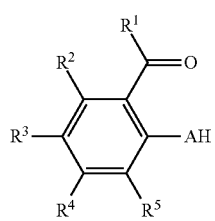

(10)

wherein $R^1$ to $R^5$ and A have the same meaning as defined for formula (7).

The compounds of formula (10) may be prepared from the corresponding precursors having at least one functional group of formula (11), formula (12) or formula (13):

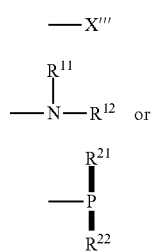

(11)
(12)
(13)

wherein $R^{11}$, $R^{12}$, $R^{21}$ and $R^{22}$ have the same meanings as defined for formula (1) or formula (2), and $X'''$ is halogen or alkylsulfonato.

The functional group of formula (11) may be converted into the functional group of formula (1) by nucleophilic displacement of $X'''$ with $NR^{11}R^{12}R^{13}$ or $PR^{11}R^{12}R^{13}$. The rate of this nucleophilic displacement reaction may be enhanced by the addition of an additive such as NaI.

The functional group of formula (12) may be converted into the functional group of formula (1) by nucleophilic attack thereon by $R^{13}$—$X'''$. Similarly, the rate of nucleophilic displacement reaction may be enhanced by the addition of an additive such as NaI.

The functional group of formula (13) may be converted into the functional group of formula (2) through a reaction with $ClN=PR^{23}R^{24}R^{25}$ using the known procedure [Grebe, J.; Schlecht, F.; Weller, F.; Harms, K.; Geiseler, G.; Dehnicke, K. *Z. Angorg. Allg. Chem.* 1999, 625, 633.].

According to another aspect of the present invention, the catalytic complex may be recovered by a process comprising the steps of treating the reaction mixture containing the polycarbonate and the complex with a composite-forming material to form a composite of the complex and the composite-forming material; removing the composite from the reaction mixture containing the polycarbonate; and recovering the complex from the composite by treating the composite in a medium which does not dissolve the composite-forming material with an acid and/or a non-reactive metal salt, and isolating the complex released into the medium.

In the present invention, "the reaction mixture containing the polycarbonate and the complex" is the reaction mixture obtained by the inventive polymerization process.

Preferably, the composite-forming material is an inorganic solid, a polymer or a mixture thereof, wherein the inorganic solid is selected from the group consisting of silica and alumina, and the polymer has at least one functional group capable of becoming an anion through deprotonation by the action of an alkoxy anion. Particularly, poly(acrylic acid) is preferable.

The composite-forming material may be preferably surface-modified or non-modified silica or alumina.

The functional group capable of becoming an anion through deprotonation by the action of an alkoxy anion may be selected from the group consisting of sulfonic acid group, carboxylic acid group, phenol group and alcohol group. Particularly, the polymer having at least one functional group capable of undergoing deprotonation by the action of an alkoxy anion may be a copolymer or a homopolymer comprising any one of following units:

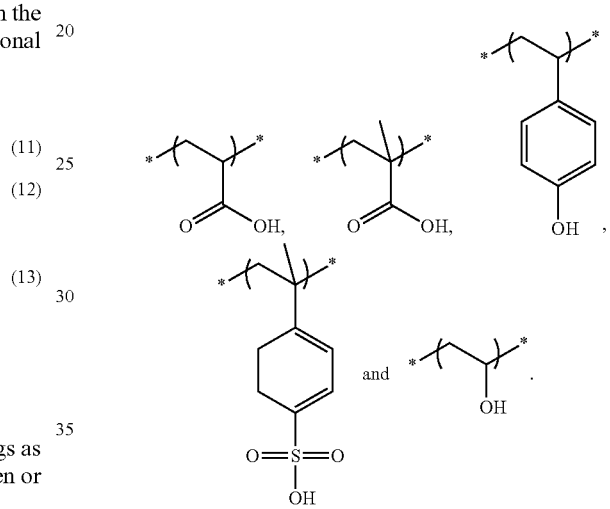

According to the preferable example of the present invention, the polymer may have a number average molecular weight of from 500 to 10,000,000 and it is preferably cross-linked. However, a polymer which is not cross-linked may be used insofar as the polymer does not dissolve into the solution containing the polycarbonate and the complex.

According to the preferable example of the present invention, the treatment of the reaction mixture with the composite-forming material may be conducted by adding the composite-forming material to the reaction mixture, and the composite formed is separated from the reaction mixture by filtration; or by passing the reaction mixture through a column filled with the composite-forming material.

FIG. 1 shows the step of treating the reaction mixture containing the polycarbonate and the complex with a composite-forming material to form a composite of the complex and the composite-forming material.

Figure 2:
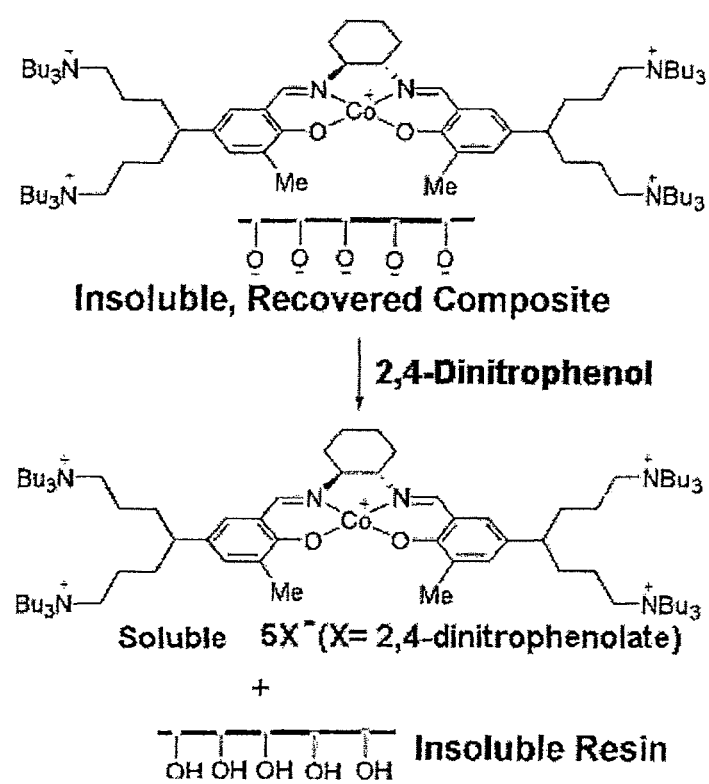
FIGS. 2 and 3: schematic diagrams illustrating mechanisms for recovering catalytic complexes.
Figure 3:
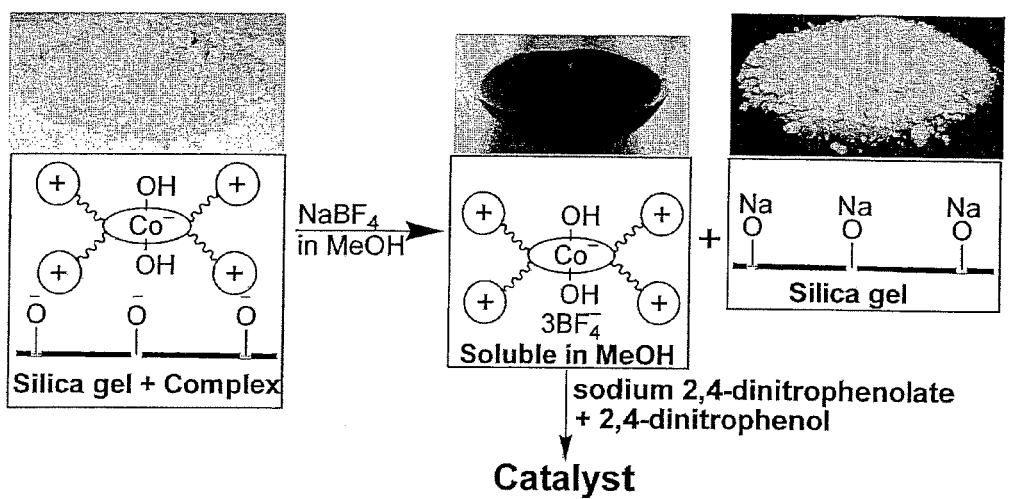

FIGS. 2 and 3 respectively show the process for recovering the complex from the composite by treating the composite of the complex and the composite-forming material in a medium which does not dissolve the composite-forming material with an acid and/or a non-reactive metal salt so that only the free complex dissolves into the medium. Preferable medium includes methylene chloride, ethanol or methanol.

Preferably, the acid may have a Pka value of lower than that of the anion formed on the composite-forming material. An acid whose conjugate base has a high polymerization activity is preferable. Particularly, hydrochloric acid and 2,4-dinitrophenol are preferable. Preferable examples of the non-reactive metal salt include M'BF$_4$ or M'ClO$_4$ (wherein M' is Li, Na or K).

Hereinafter, the present invention will be described in more detail with reference to the following examples. However, these examples are given for the purpose of illustration only, and are not intended to limit the scope of the invention.

Example 1

Preparation of the complex of formula (6a)

mL of water was added thereto, and stirred for 4 hours. The resulting solution was extracted with ethyl acetate. The separated organic layer was dried over anhydrous magnesium sulfate, and filtered. The solvent was removed from the filtrate using a rotary vacuum evaporator, and the residue was purified by column chromatography using a 1:20 mixture of ethyl acetate and hexane, to obtain 2-tert-butyl-4-(3-chloropropyl)dimethylsilylphenol (yield: 84%). IR (KBr): 3533 (OH) cm$^{-1}$. $^1$H NMR (CDCl$_3$): δ 7.41 (s, 1H, m-H), 7.22 (dd, J=7.6 Hz, 1.2 Hz, 1H, m-H), 6.68 (d, J=7.6 Hz, 1H, o-H), 4.85 (s, 1H, OH), 3.52 (t, J=7.2 Hz, 2H, CH$_2$Cl), 1.81 (m, 2H, CH$_2$CH$_2$CH$_2$), 1.45 (s, 9H, tert-BuCH$_3$), 0.86 (m, 2H, CH$_2$Si), 0.30 (s, 6H, CH$_3$) ppm. $^{13}$C {$^1$H}NMR (CDCl$_3$): δ 154.94, 135.23, 132.47, 132.09, 129.12, 116.14, 48.08, 34.67, 29.68, 27.81, 13.86, −2.72 ppm. HRMS (FAB): m/z calculated ([M]C$_{15}$H$_{25}$ClOSi) 284.1363. found 284.1363.

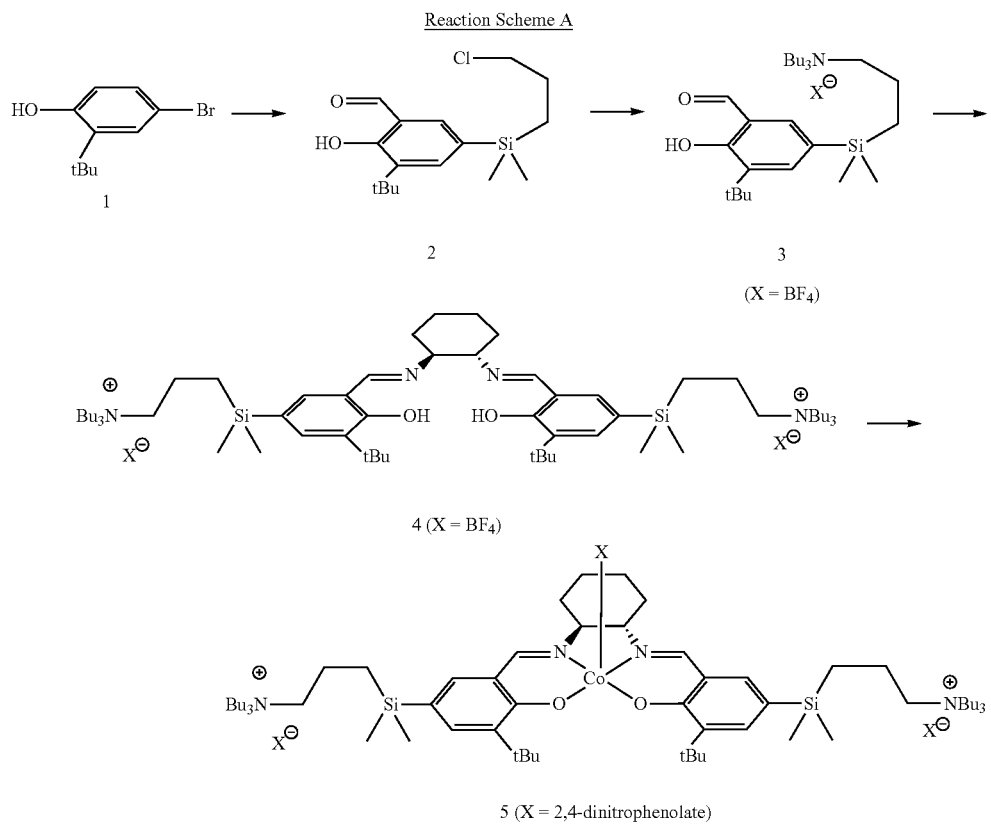

2-tert-Butyl-4-(3-chloropropyl)dimethylsilylphenol (2.72 g, 9.90 mmol) thus obtained was dissolved in tetrahydrofuran (180 mL), and added thereto were paraformaldehyde (1.16 g, 35.6 mmol), triethylamine (4.01 g, 35.6 mmol) and magnesium chloride (3.77 g, 35.6 mmol). The resulting mixture was refluxed for 3 hours under a nitrogen atmosphere, when color of the mixture gradually turned yellow. After the reaction was completed, the reaction solution was cooled to room temperature, the solvent was removed therefrom and the resulting residue was treated with ethyl acetate and water. The organic layer was separated, dried over anhydrous magnesium sulfate, and filtered. The solvent of the filtrate was removed using a rotary vacuum evaporator, and the residue was purified by column chromatography using 1:20 mixture of ethyl acetate and hexane to obtain Compound 2. $^1$H NMR (CDCl$_3$): δ 11.87 (s, 1H, OH), 9.91 (s, 1H, CHO), 7.64 (d, J=1.6 Hz, 1H, (1) Synthesis of Compound 1

2-tert-Butylphenol (40 g, 266 mmol) was dissolved in carbon disulfide (50 mL), and bromine (42.6 g, 266 mmol) was slowly added thereto over 2 hours using a dropping funnel while stirring at 0° C. After allowing the reaction to proceed for 12 hours, the solvent was removed using a rotary vacuum evaporator. The residue was distilled under a reduced pressure at 65-68° C. to obtain Compound 1 (yield: 90%).

(2) Synthesis of Compound 2

Compound 1 (2.7 g, 12 mmol) was dissolved in tetrahydrofuran (100 mL) under a nitrogen atmosphere, and tert-BuLi (14.5 g, 1.7 M pentane solution) was added thereto using a syringe while stirring at −78° C. The reaction was allowed to proceed at −78° C. for 2 hours, and chloro(3-chloropropyl)dimethylsilane (4.639 g, 27.1 mmol) was added to the reaction mixture using a syringe. The resulting solution was slowly warmed to room temperature over 2 hours, 150 m-H), 7.53 (d, J=1.6 Hz, 1H, m-H), 3.53 (t, J=7.2 Hz, 2H, CH$_2$Cl), 1.81 (m, 2H, CH$_2$), 1.46 (s, 9H, CH$_3$), 0.91 (m, 2H, CH$_2$Si), 0.35 (s, 6H, CH$_3$) ppm. $^{13}$C {$^1$H}NMR (CDCl$_3$): δ 197.14, 161.68, 138.35, 137.76, 137.20, 127.93, 120.34, 47.85, 34.92, 29.27, 27.61, 13.49, −2.90 ppm. HRMS (FAB): m/z calculated ([M+H]$^+$ C$_{16}$H$_{26}$ClO$_2$Si) 313.1391. found 313.1391.

(3) Synthesis of Compound 3

Compound 2 (1.00 g, 3.21 mmol), tributylamine (0.891 g, 4.81 mmol) and sodium iodide (0.720 g, 4.81 mmol) were dissolved in acetonitrile (5 mL) under a nitrogen atmosphere and stirred at 90° C. for a day. The resulting solution was cooled to room temperature, treated with water and methylene chloride, and the organic and aqueous layers were separated. The aqueous layer was extracted with methylene chloride. The above procedure was repeated to enhance the yield of the final product. The combined organic layer was dried over anhydrous magnesium sulfate and filtered. After removing the solvent from the filtrate, diethyl ether was added to the resulting residue, the diethylether separated, and diethyl ether was removed to obtain an oily material. The oil was dissolved in ethanol, and AgBF$_4$ (0.686 g, 3.52 mmol) was slowly added thereto, stirred at room temperature for 1 hour, the solvent was removed, and the resulting residue treated with methylene chloride (10 mL) and water (10 mL). The organic layer was separated, dried over anhydrous magnesium sulfate, and filtered. The solvent was removed from the filtrate, and the residue was purified by column chromatography (methylene chloride:ethanol=10:1) to obtain Compound 3 (yield: 56%). $^1$H NMR (CDCl$_3$): δ 11.92 (s, 1H, OH), 9.96 (s, 1H, CHO), 7.67 (s, 1H, m-H), 7.59 (s, 1H, m-H), 3.24-3.08 (m, 8H, NCH$_2$), 1.79-1.50 (m, 8H, CH$_2$), 1.42 (s, 9H, CH$_3$), 1.43-1.30 (m, 6H, CH$_2$), 1.04-0.86 (m, 9H, CH$_3$), 0.72-0.78 (t, J=8.4 Hz, 2H, CH$_2$Si), 0.34 (s, 6H, CH$_3$Si) ppm. $^{13}$C {$^1$H}NMR (CDCl$_3$): δ 198.12, 161.73, 138.39, 138.08, 137.18, 127.04, 120.49, 61.10, 58.29, 34.90, 29.25, 23.75, 19.59, 16.69, 13.59, 12.23, −3.15 ppm. HRMS (FAB): m/z calculated ([M-BF$_4$—]$^+$ C$_{28}$H$_{52}$NO$_2$Si) 462.3762. found 462.3767.

(4) Synthesis of Compound 4

Compound 3 (0.212 g, 0.368 mmol) and trans-1,2-diaminocyclohexane (0.20 g, 0.18 mmol) were dissolved in ethanel (2 mL) under a nitrogen atmosphere, molecular sieve was added thereto, and stirred at room temperature for 10 hours. The solvent was removed to obtain a yellow solid, which was purified by column chromatography (methylene chloride:ethanol=10:1) to obtain Compound 4. IR (KBr): 3421 (OH), 1625 (C=N) cm$^{-1}$. $^1$H NMR (CDCl$_3$): δ 14.16 (s, 2H, OH), 8.42 (s, 2H, CH=N), 7.32 (s, 2H, m-H), 7.21 (s, 2H, m-H), 3.40 (t, J=4.0 Hz, 2H, CHN), 3.11 (t, J=8.0 Hz, 16H, NCH$_2$), 2.04-1.96 (m, 2H, cyclohexyl-CH$_2$), 1.92-1.87 (m, 2H, cyclohexyl-CH$_2$), 1.74-1.68 (m, 4H, cyclohexyl-CH$_2$), 1.58-1.40 (m, 16H, NCH$_2$CH$_2$), 1.41 (s, 18H, tert-BuCH$_3$) 1.32 (sextet, J=7.2 Hz, 12H, NCH$_2$CH$_2$CH$_2$), 0.90 (t, J=7.6 Hz, 18H, CH$_3$), 0.70 (t, J=8.0 Hz, 4H, SiCH$_2$), 0.26 (s, 6H, SiCH$_3$), 0.25 (s, 6H, SiCH$_3$) ppm. $^{13}$C {$^1$H}NMR (CDCl$_3$): δ165.35, 161.39, 136.34, 135.68, 133.46, 124.69, 118.48, 71.70, 60.95, 58.21, 34.81, 32.73, 29.38, 24.03, 23.65, 19.53, 16.72, 13.54, 12.24, −2.94, −3.22 ppm. HRMS (FAB): m/z calculated ([M-BF$_4$]$^+$ C$_{62}$H$_{114}$N$_4$O$_2$Si$_2$BF$_4$) 1089.8504. found 1089.8521.

(5) Synthesis of Compound 5

Upon dissolving Co(OAc)$_2$ (0.022 g, 0.13 mmol)) and Compound 4 (0.147 g, 0.125 mmol) in ethanol (6 mL) under a nitrogen atmosphere, a red solid was formed while the color of the solvent changed to red. After further stirring for 2 hours, the red solid was filtered, washed twice with ethanol (2 mL), and dried in a vacuum. The resulting solid and 2,4-dinitrophenol (23 g, 0.125 mmol) were dissolved in methylene chloride and stirred for 1.5 hours under an oxygen atmosphere. Sodium 2,4-dinitrophenoxide (0.051 g, 0.25 mmol) was added thereto, and stirred overnight. The resulting solution was filtered through cellite, and the solvent was removed from the filtrate to obtain Compound 5 as a solid. $^1$H NMR (dmso-d$_6$): δ 8.58 (d, J=0.8 Hz, 3H, (NO$_2$)$_2$C$_6$H$_3$O), 7.90 (s, 2H, CH=N), 7.75 (dd, J=9.6, 3.2 Hz, 3H, (NO$_2$)$_2$C$_6$H$_3$O), 7.68 (s, 2H, m-H), 7.45 (s, 2H, m-H), 6.30 (d, J=9.6, 3H, (NO$_2$)$_2$C$_6$H$_3$O), 3.63-3.57 (br, 2H, cyclohexyl-CH), 3.23-3.12 (m, 12H, NCH$_2$), 3.12-3.02 (m, 4H, NCH$_2$), 2.08-1.96 (br, 4H, cyclohexyl-CH$_2$), 1.96-1.82 (br, 4H, cyclohexyl-CH$_2$), 1.74 (s, 18H, CH$_3$) 1.70-1.52 (m, 12H, butyl-CH$_2$), 1.36-1.25 (m, 12H, butyl-CH$_2$), 0.92 (t, J=7.6 Hz, 18H, CH$_3$), 0.71 (t, J=8.0, 4H, SiCH$_2$), 0.30 (s, 3H, SiCH$_3$), 0.29 (s, 3H, SiCH$_3$) ppm. $^{13}$C {$^1$H}NMR (dmso-d$_6$): δ 169.79, 164.93, 164.40, 141.64, 140.23, 134.89, 127.07, 126.15, 124.70, 120.92, 119.15, 69.30, 60.34, 57.39, 35.55, 30.25, 29.51, 24.18, 23.02, 19.17, 16.32, 13.43, 11.91, −2.66, −2.74 ppm. HRMS (FAB): m/z calculated ([M−2 {(NO$_2$)$_2$C$_6$H$_{30}$}]$^+$ C$_{68}$H$_{115}$CoN$_6$O$_7$Si$_2$) 1242.7687. found 1242.7698.

Example 2

Preparation of the complex of formula (6b)

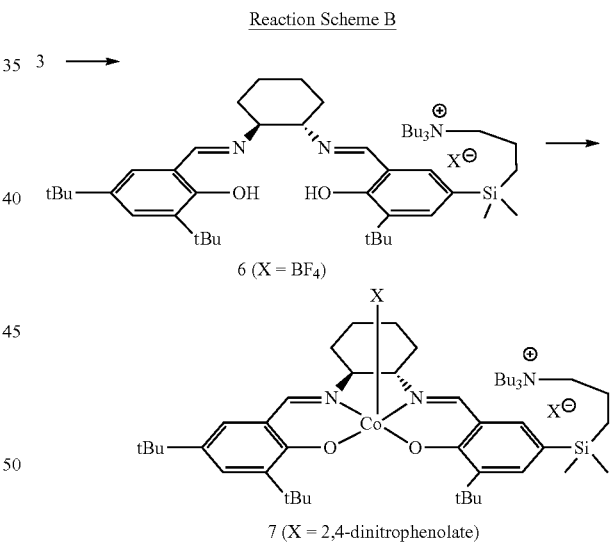

Reaction Scheme B 6 (X = BF$_4$)

7 (X = 2,4-dinitrophenolate)

(1) Synthesis of Compound 6

Compound 6 was synthesized from Compound 3 by using the known procedure [T. V. Hansen, L. Skattebøl, *Tetrahedron Lett.* 2005, 46, 3829]. The resulting product was purified by column chromatography using a 40:1 mixture of methylene chloride and ethanol to obtain Compound 6. IR (KBr): 3409 (OH), 1627 (C=N) cm$^{-1}$. $^1$H NMR (CDCl$_3$): δ 14.16 (s, 1H, OH), 13.62 (s, 1H, OH), 8.36 (s, 1H, CH=N), 8.32 (s, 1H, CH=N), 7.30 (d, J=2.4 Hz, 1H, m-H), 7.29 (d, J=1.6 Hz, 1H, m-H), 7.16 (d, J=1.6 Hz, 1H, m-H), 6.99 (d, J=2.4 Hz, 1H, m-H), 3.42-3.32 (m, 2H, CHN), 3.30 (t, J=8.4 Hz, 8H, NCH$_2$), 2.13-1.56 (m, 8H, cyclohexyl-CH$_2$), 1.68-1.55 (m, 8H, NCH$_2$CH$_2$), 1.41 (s, 9H, tert-BuCH$_3$), 1.40 (s, 9H, tert-BuCH$_3$), 1.39-1.34 (m, 6H, NCH$_2$CH$_2$CH$_2$), 1.24 (s, 9H, tert-BuCH$_3$), 0.93 (t, J=7.2 Hz, 9H, CH$_3$), 0.77-0.71 (m, 2H, SiCH$_2$), 0.27 (s, 3H, SiCH$_3$), 0.25 (s, 3H, SiCH$_3$) ppm. $^{13}$C {$^1$H}NMR (CDCl$_3$): δ 165.45, 165.08, 161.48, 157.67, 139.73, 136.54, 136.08, 135.57, 133.36, 126.58, 125.83, 124.51, 118.49, 117.63, 72.43, 72.14, 61.64, 59.03, 34.99, 34.84, 34.08, 33.31, 31.45, 29.47, 29.40, 24.34, 24.22, 19.80, 17.24, 13.72, 12.67, −2.88, −2.98 ppm. HRMS (FAB): m/z calculated ([M-BF$_4^-$]$^+$ C$_{49}$H$_{84}$N$_3$O$_2$Si) 774.6327. found 774.6333.

(2) Synthesis of Compound 7

The procedure for synthesizing Compound 5 was repeated except that Compound 6 was used instead of Compound 4 to obtain Compound 7. $^1$H NMR (dmso-d$_6$): δ 8.69 (br, 2H, (NO$_2$)$_2$C$_6$H$_3$O), 7.88 (s, 2H, CH=N), 7.81 (br, 2H, (NO$_2$)$_2$C$_6$H$_3$O), 7.69 (s, 1H, m-H), 7.47 (s, 1H, m-H), 7.45 (s, 2H, m-H), 6.36 (br, 2H, (NO$_2$)$_2$C$_6$H$_3$O), 3.65-3.59 (m, 2H, CHN), 3.26-3.14 (m, 6H, NCH$_2$), 3.12-3.04 (m, 2H, NCH$_2$), 2.08-1.96 (m, 4H, cyclohexyl-CH$_2$), 1.96-1.82 (m, 4H, cyclohexyl-CH$_2$), 1.76 (s, 9H, tert-BuCH$_3$), 1.74 (s, 9H, tert-BuCH$_3$), 1.65-1.52 (m, 8H, NCH$_2$CH$_2$), 1.31 (s, 9H, tert-BuCH$_3$), 1.32-1.26 (m, 6H, NCH$_2$CH$_2$CH), 0.92 (t, J=7.2 Hz, 9H, CH$_3$), 0.72 (t, J=8.0 Hz, 2H, SiCH$_2$), 0.30 (s, 6H, SiCH$_3$) ppm. $^{13}$C {$^1$H}NMR (dmso-d$_6$): δ171.30, 164.92, 164.25, 164.03, 163.73, 161.46, 141.53, 141.38, 140.01, 135.63, 134.57, 128.84, 128.52, 127.28, 124.84, 120.54, 119.12, 118.15, 69.12, 69.05, 60.24, 59.69, 57.28, 35.58, 35.40, 33.33, 31.24, 30.22, 30.10, 29.35, 28.46, 24.07, 22.89, 19.04, 16.20, 13.88, 13.28, 11.81, −0.05, −2.80, −2.85 ppm. HRMS (FAB): m/z calculated ([M-{(NO$_2$)$_2$C$_6$H$_{3O}$}]$^+$ C$_{49}$H$_{82}$CoN$_3$O$_2$Si) 831.5503. found 831.5508.

Example 3

Preparation of the complex of formula (6c)

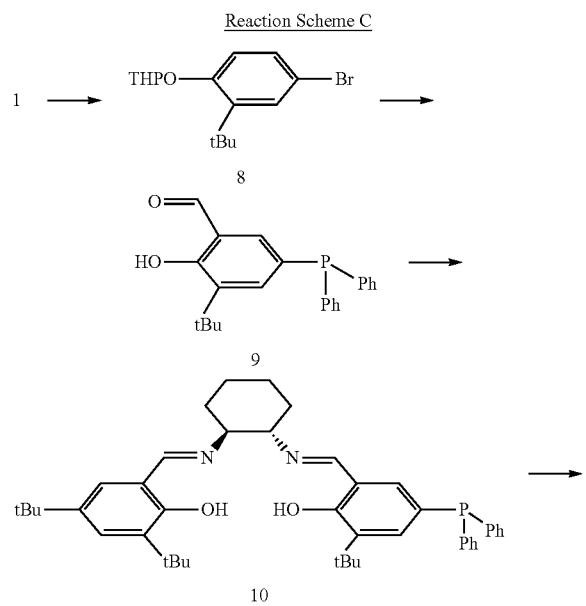

Reaction Scheme C (1) Synthesis of Compound 8

Compound 1 (15 g, 65.5 mmol), dihydropyran (6.33 g, 75.3 mmol) and pyridinium p-toluenesulfonate (0.200 g) were dissolved in methylene chloride under a nitrogen atmosphere. The solution was stirred at room temperature for 19 hours. The solvent was removed and the residue was recrystallized with hexane to obtain Compound 8 as a white solid (yield: 72%).

(2) Synthesis of Compound 9

Compound 8 (14.6 g, 46.7 mmol) was dissolved in tetrahydrofuran (300 mL) at −78° C. under a nitrogen atmosphere, and n-BuLi (14.23 g, 51.34 mmol, 2.5 M hexane solution) was added thereto using a syringe. The reaction was allowed to proceed for 2 hours while stirring, and chlorodiphenylphosphine (10.3 g, 46.7 mmol) was added to the reaction mixture using a syringe. The resulting solution was slowly warmed to room temperature while stirring over 2 hours. The resulting solution was treated with ethyl acetate (100 mL) and water (100 mL). The organic layer was separated, dried over anhydrous magnesium sulfate, and filtered. The solvent was removed from the filtrate, and the residue was recrystallized with hexane to obtain Compound 9 as a solid (yield: 80%). $^1$H NMR (CDCl$_3$): δ 7.39 (s, 1H), 7.37 (s, 1H), 7.35 (s, 9H, Ph), 7.19 (d, $^2$J$_{PH}$=8.0 Hz, 1H, m-H), 7.11 (dd, $^2$J$_{PH}$=8.0 Hz, J$_{HH}$=6.8 Hz, 1H), 5.53 (br, 1H, THP), 3.93 (td, J=10.0 Hz, 2.4 Hz, 1H, THP), 3.72-3.65 (m, 1H, THP), 2.15-2.02 (m, 1H, THP), 2.92-1.90 (m, 2H, THP), 1.83-1.71 (m, 2H, THP), 1.71-1.62 (m, 1H, THP), 1.41 (s, 9H, tert-BuCH$_3$) ppm. $^{13}$C {$^1$H}NMR (CDCl$_3$): δ 156.59, 138.02 (d, $^3$J$_{CP}$=3.8 Hz, m-Ph), 137.92 (d, $^3$J$_{CP}$=3.7 Hz, m-Ph), 137.71 (d, $^1$J$_{CP}$=9.1 Hz, PC), 133.29 (d, $^2$J$_{CP}$=18.2 Hz, o-Ph), 133.28 (d, $^2$J$_{CP}$=18.9 Hz, o-Ph), 133.00, 132.79 (d, $^2$J$_{CP}$=12.1 Hz, m-C), 128.19, 128.16 (d, $^2$J$_{CP}$=6.8 Hz, m-C), 127.19 (d, $^3$J$_{CP}$=6.0 Hz, o-C), 114.32 (d, $^3$J$_{CP}$=5.8 Hz, o-C), 61.89, 35.04, 30.57, 29.96, 25.31, 19.01 ppm. $^{31}$P NMR (CDCl$_3$): δ 11.53 ppm. Anal. Calc. (C$_{27}$H$_{31}$O$_2$P): C, 77.49; H, 7.47%. found: C, 77.68; H, 7.60%.

The resulting solid (15.60 g, 37.28 mmol) and pyridium p-toluene sulfonate (9.36 g, 37.28 mmol) were dissolved in a mixture of tetrahydrofuran (60 mL) and ethanol (40 mL), and the resulting mixture was stirred at 80-90° C. overnight. The reaction solution was treated with sodium hydrogen carbonate and ethyl acetate. The organic layer was separated, dried over anhydrous magnesium sulfate, and filtered. The solvent was removed from the filtrate, and purified by column chromatography to obtain 2-tert-butyl-4-diphenylphosphanylphenol. IR (KBr): 3307 (OH) cm$^{-1}$. $^1$H NMR (CDCl$_3$): δ 7.41 (dd, $^2J_{PH}$=9.2 Hz, $J_{HH}$=1.6 Hz, 1H, m-H), 7.40-7.34 (m, 10H, Ph), 7.04 (ddd, $^2J_{PH}$=9.2 Hz, $J_{HH}$=7.6 Hz, 1.6 Hz, 1H, m-H), 6.69 (d, J=7.6 Hz, 1H, o-H), 5.27 (s, 1H, OH), 1.42 (s, 9H, tert-BuCH$_3$) ppm. $^{13}$C {$^1$H}NMR (CDCl$_3$): δ 155.06, 137.76 (d, $^1J_{CP}$=9.8 Hz, PC), 136.08 (d, $^2J_{CP}$=9.1 Hz, PC), 133.55 (d, $^2J_{CP}$=28 Hz, m-C), 133.21 (d, $^2J_{CP}$=18 Hz, o-Ph), 132.68 (d, $^2J_{CP}$=28 Hz, m-C), 128.28, 128.20 (d, $^3J_{CP}$=6.9 Hz, m-Ph), 126.64 (d, $^3J_{CP}$=6.1 Hz, o-C), 116.91 (d, $^3J_{CP}$=6.1 Hz, o-C), 34.73, 29.53 ppm. $^{31}$P NMR (CDCl$_3$): δ 11.44 ppm. Anal. Calc. (C$_{22}$H$_{23}$OP): C, 79.02; H, 6.93; 0, 4.78; P, 9.26%. found: C, 79.29; H, 7.05%.

The procedure for synthesizing Compound 2 was repeated except that 2-tert-butyl-4-diphenylphosphanylphenol was used instead of 2-tert-butyl-4-(3-chloropropyl)dimethylsilylphenol, to obtain Compound 9. IR (KBr): 3390 (OH), 1649 (C=O) cm$^{-1}$. $^1$H NMR (CDCl$_3$): δ 11.87 (s, 1H, OH), 9.70 (s, 1H, CHO), 7.51 (d, $^2J_{PH}$=8.4 Hz, 1H, m-H), 7.40-7.20 (m, 11H, P-Ph), 1.34 (s, 9H, tert-BuCH$_3$) ppm. $^{13}$C {$^1$H}NMR (CDCl$_3$): δ 196.85, 161.64, 139.44 (d, $^2J_{CP}$=24.3 Hz, m-C), 138.38 (d, $^3J_{CP}$=6.8 Hz, o-C), 137.67 (d, $^2J_{CP}$=18.2 Hz, m-C), 136.90 (d, $^1J_{CP}$=10.6 Hz, C—P), 133.20 (d, $^2J_{CP}$=19 Hz, o-Ph), 128.66, 128.43 (d, $^3J_{CP}$=6.1 Hz, m-Ph), 126.50 (d, $^1J_{CP}$=10.6 Hz, C—P), 120.73 (d, $^3J_{CP}$=6.1 Hz, o-C), 35.06, 29.16 ppm. $^{31}$P NMR (CDCl$_3$): δ 10.99 ppm. Anal. Calc. (C$_{23}$H$_{23}$O$_2$P): C, 76.23; H, 6.40; O, 8.83; P, 8.55%. found: C, 76.03; H, 6.08%.

(3) Synthesis of Compound 10

Compound 10 was synthesized from Compound 9 by using the known procedure [T. V. Hansen, L. Skattebøl, *Tetrahedron Lett.* 2005, 46, 3829.]. IR (KBr): 3407 (OH), 1627 (C=N) cm$^{-1}$. $^1$H NMR(C$_6$D$_6$): δ 14.61 (s, 1H, OH), 13.96 (s, 1H, OH), 7.90 (s, 1H, CH=N), 7.64 (dd, $J_{HH}$=8.8 Hz, $^2J_{PH}$=1.6 Hz, 1H, m-H), 7.58 (s, 1H, CH=N), 7.51 (d, $J_{HH}$=2.4 Hz, 1H), 7.46-7.35 (m, 4H, Ph), 7.14-7.04 (m, 7H, Ph), 6.97 (d, J=2.4 Hz, 1H, m-H), 2.91-2.82 (m, 1H, NCH), 2.74-2.67 (m, 1H, NCH), 1.69-1.62 (br, 2H, cyclohexyl-CH$_2$), 1.62 (s, 9H, tert-BuCH$_3$), 1.54-1.50 (br, 2H, cyclohexyl-CH$_2$), 1.47 (s, 9H, tert-BuCH$_3$), 1.37-1.31 (br, 2H, cyclohexyl-CH$_2$), 1.29 (s, 9H, tert-BuCH$_3$), 1.16-1.08 (br, 2H, cyclohexyl-CH$_2$) ppm. $^{13}$C {$^1$H}NMR (CDCl$_3$): δ 166.31, 165.78, 161.98, 158.59, 140.06, 138.91 (d, $^2J_{CP}$=19.7 Hz), 138.79 (d, $^2J_{CP}$=19.7 Hz), 137.98 (d, $^1J_{CP}$=8.3 Hz), 136.79, 136.49, 136.20 (d, $^2J_{CP}$=24.3 Hz), 135.80, 133.90 (d, $^1J_{CP}$=8.3 Hz), 133.70 (d, $^3J_{PC}$=7.6 Hz), 128.79 (d, $^3J_{CP}$=3.7 Hz), 128.73 (d, $^3J_{CP}$=3.0 Hz), 128.60 (d, $J_{CP}$=8.4 Hz), 127.02, 126.44, 125.04 (d, $J_{CP}$=8.3 Hz), 119.54 (d, $^3J_{CP}$=6.8 Hz), 118.41, 72.22, 71.55, 35.52, 35.41, 34.38, 33.07, 32.97, 31.86, 29.94, 29.66, 24.56 ppm. $^{31}$P NMR (CDCl$_3$): δ 11.66 ppm. Anal. Calc. (C$_{44}$H$_{55}$N$_2$O$_2$P): C, 78.30; H, 8.21; N, 4.15; 0, 4.74; P, 4.59%. found: C, 78.51; H, 8.32%.

(4) Synthesis of Compound 11

Compound 11 was synthesized from Compound 10 by using the procedure. [J. Grebe, F. Schlecht, F. Weller, K. Harms, G. Geiseler, K. Dehnicke, *Z. Angorg. Allg. Chem.* 1999, 625, 633.](yield: 79%). IR (KBr): 3367 (OH), 1629 (C=N) cm$^{-1}$. $^1$H NMR (CDCl$_3$): δ 15.16 (s, 1H, OH), 13.48 (s, 1H, OH), 8.39 (s, 1H, CH=N), 8.09 (s, 1H, CH=N), 7.67-7.61 (m, 2H), 7.60-7.52 (m, 4H), 7.52-7.38 (m, 19H), 7.34 (d, J=2.4 Hz, 1H), 7.31 (dd, J=13.2 Hz, J=2.0 Hz, 1H), 7.06 (d, J=2.0 Hz, 1H), 6.81 (dd, J=13.2 Hz, J=1.6 Hz, 1H), 3.42-3.38 (m, 2H, CHN), 2.02-1.88 (m, 6H, cyclohexyl-CH$_2$), 1.73 (br, 2H, cyclohexyl-CH$_2$), 1.37 (s, 9H, tert-BuCH$_3$), 1.27 (s, 9H, tert-BuCH$_3$), 1.18 (s, 9H, tert-BuCH$_3$) ppm. $^{13}$C {$^1$H}NMR (CDCl$_3$): δ 167.32, 165.95, 164.16, 157.98, 140.40, 140.19 (d, $J_{CP}$=12.1 Hz), 136.71, 135.56 (d, $J_{CP}$=13.6 Hz), 133.90, 132.11 (d, $J_{CP}$=10.6 Hz), 131.97 (d, $J_{CP}$=3.0 Hz), 131.76 (d, $J_{CP}$=12.1 Hz), 129.65 (d, $J_{CP}$=12.8 Hz), 128.19 (d, $J_{CP}$=9.1 Hz), 127.80, 127.06, 126.74, 126.20, 118.36 (d, $J_{CP}$=15.1 Hz), 117.92, 113.31, 112.19, 72.78, 71.44, 35.45, 35.34, 34.48, 33.65, 33.59, 31.80, 29.76, 29.18, 24.58, 24.51 ppm. $^{31}$P NMR (CDCl$_3$): 38.81 (d, $J_{PP}$=55.0 Hz), 33.80 (d, $J_{PP}$=55.0 Hz) ppm. HRMS (FAB): m/z calculated ([M-Cl]$^+$ C$_{62}$H$_{70}$N$_3$O$_2$P$_2$) 950.4938. found 950.4943.

(5) Synthesis of Compound 12

Compound 11 (0.046 g, 0.047 mmol) and AgBF$_4$ (0.011 g, 0.56 mmol) were added in ethanol and stirred at room temperature overnight. The resulting solution was filtered through cellite, and the solvent was removed from the filtrate. The procedure for synthesizing Compound 5 was repeated to obtain Compound 12. $^1$H NMR (dmso-d$_6$): δ 8.80 (br, 2H, (NO$_2$)$_2$C$_6$H$_3$O), 7.91-7.40 (m, 32H), 6.80 (s, 1H), 6.51 (br, 2H, (NO$_2$)$_2$C$_6$H$_3$O), 3.06 (d, J=9.2 Hz, 1H, CHN), 2.93 (d, J=9.2 Hz, 1H, CHN), 1.98-1.80 (m, 6H, cyclohexyl-CH$_2$), 1.73 (s, 9H, tert-BuCH$_3$), 1.41-1.48 (m, 2H, cyclohexyl-CH$_2$), 1.49 (s, 9H, tert-BuCH$_3$), 1.29 (s, 9H, tert-BuCH$_3$) ppm. $^{13}$C {$^1$H}172.39, 169.37, 165.70, 165.50, 162.12, 144.24 (d, $J_{CP}$=11.4 Hz), 142.35, 141.00, 137.05, 135.22 (d, $J_{CP}$=2.2 Hz), 134.16, 133.88, 133.28 (d, $J_{CP}$=11.3 Hz), 132.58 (d, $J_{CP}$=11.4 Hz), 132.49, 132.36, 130.38 (d, $J_{CP}$=12.9 Hz), 130.05 (d, $J_{CP}$=12.9 Hz), 129.29, 128.39, 127.37, 126.03, 124.34, 123.32, 120.93 (d, $J_{CP}$=15.1 Hz), 118.88, 109.57, 108.44, 70.58, 70.26, 36.63, 36.60, 34.43, 32.20, 31.22, 30.57, 30.33, 29.50, 24.99, 21.95 ppm. $^1$P NMR (dmso-d$_6$): δ 42.2, 41.89 ppm. HRMS (FAB): m/z calculated ([M-{(NO$_2$)$_2$C$_6$H$_3$O}]$^+$C$_{62}$H$_{68}$CoN$_3$O$_2$P$_2$) 1007.4113. found 1007.4119.

Example 4

Preparation of the complex of formula (6d)

Reaction Scheme D

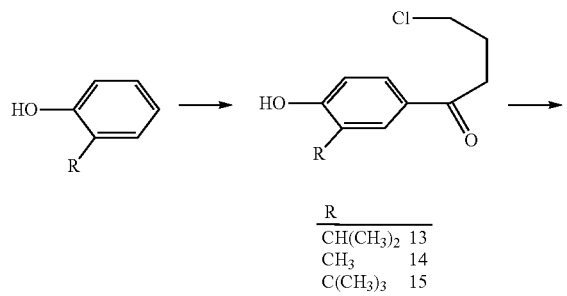

| R | |
|---|---|
| CH(CH$_3$)$_2$ | 13 |
| CH$_3$ | 14 |
| C(CH$_3$)$_3$ | 15 |

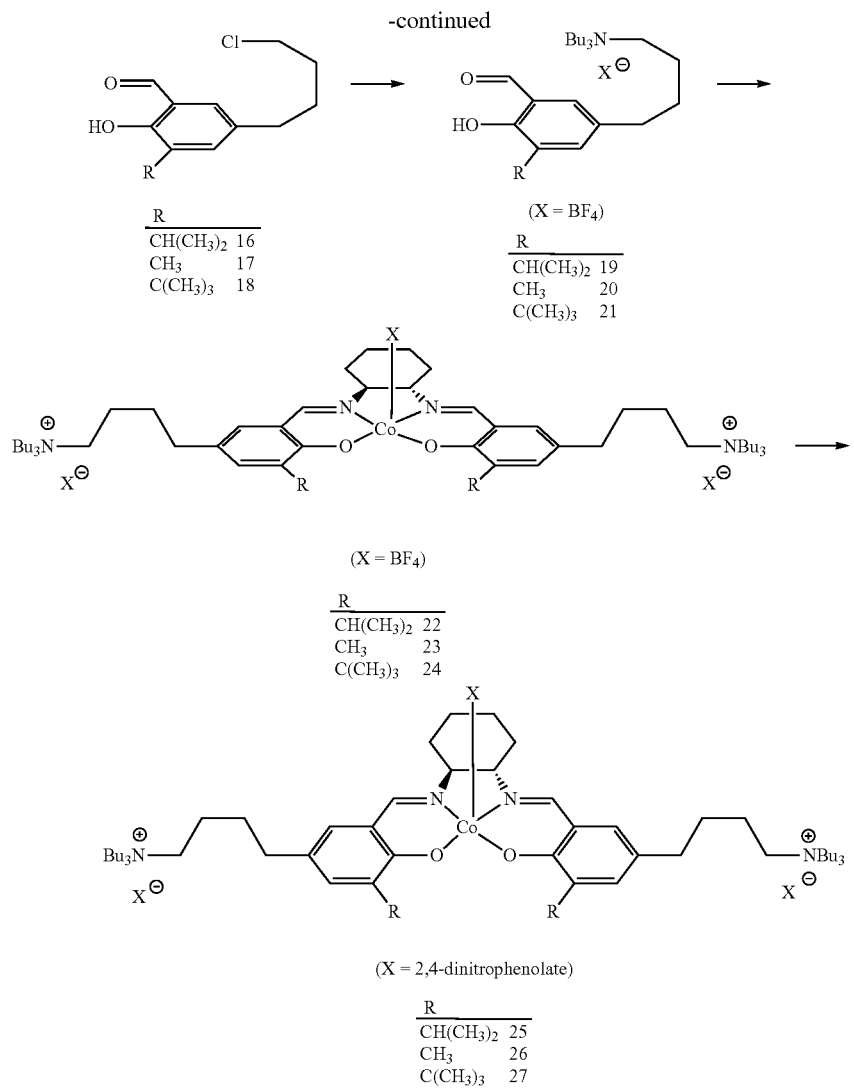

(1) Synthesis of Compound 13

AlCl₃ (1.47 g, 11.01 mmol) and 4-chlorobutyryl chloride (1.04 g, 7.34 mmol) were dissolved in methylene chloride under a nitrogen chloride atmosphere. 2-Isopropylphenol (1.00 g, 7.34 mmol) was slowly added thereto at 20° C. over 30 minutes, stirred for 3 hours, and 2 N HCl was added thereto. The resulting solution was treated with methylene chloride and water. The organic layer was separated, dried over anhydrous magnesium sulfate, and filtered. The solvent was removed from the filtrate, the residue was dissolved in methanol (10 mL), and sodium hydrogen carbonate was added thereto. The solvent was removed using a rotary vacuum evaporator, and the residue was purified by column chromatography to obtain Compound 13 (yield: 63%). $^1$H NMR (CDCl₃): δ 7.91 (d, J=2.0 Hz, 1H, m-H), 7.50 (dd, J=8.4, 2.0 Hz, 1H, m-H), 6.86 (d, J=8.4 Hz, 1H, o-H), 6.12 (s, 1H, OH), 3.69 (t, J=6.4 Hz, 2H, —CH₂Cl), 3.29 (septet, J=6.8 Hz, 1H, iPr-CH), 3.18 (t, J=6.8 Hz, 2H, —CH₂), 2.25 (quintet, J=6.4 Hz, 2H, —CH₂—), 1.30 (d, J=8.4 Hz, 6H, iPr-CH₃) ppm. $^{13}$C {$^1$H}NMR (CDCl₃): δ198.77, 158.00, 134.87, 129.50, 127.87, 127.17, 115.06, 44.81, 35.06, 27.29, 27.14, 22.44 ppm.

(2) Synthesis of Compound 14

The procedure for synthesizing Compound 13 was repeated except that 2-methylphenol was used instead of isopropylphenol to obtain Compound 14. $^1$H NMR (CDCl₃): δ 7.82 (d, J=2.0 Hz, 1H, m-H), 7.77 (dd, J=8.0, 2.0 Hz, 1H, m-H), 6.90 (s, 1H, OH), 6.88 (d, J=8.0 Hz, 1H, o-H), 3.68 (t, J=6.4 Hz, 2H, —CH₂Cl), 3.17 (t, J=6.4 Hz, 2H, —CH₂), 2.32 (s, 3H, —CH₃), 2.24 (quintet, J=6.4 Hz, 2H, —CH₂) ppm. $^{13}$C {$^1$H}NMR (CDCl₃): δ 198.81, 159.04, 131.56, 129.13, 128.17, 124.37, 114.71, 44.79, 35.10, 27.17, 16.00 ppm.

(3) Synthesis of Compound 15

The procedure for synthesizing Compound 13 was repeated except that 2-tert-butylphenol was used instead of isopropylphenol to obtain Compound 15. $^1$H NMR (CDCl₃): δ 7.99 (d, J=2.0 Hz, 1H, m-H), 7.76 (dd, J=8.4, 2.0 Hz, 1H, m-H), 6.81 (d, J=8.4 Hz, 1H, o-H), 6.70 (s, 1H, OH), 3.69 (t, J=6.4 Hz, 2H, —CH₂Cl), 3.17 (t, J=7.2 Hz, 2H, —CH₂), 2.25 (quintet, J=6.0 Hz, 2H, —CH₂—), 1.45 (s, 9H, —C(CH₃)₃), ppm. $^{13}$C {$^1$H}NMR (CDCl₃): δ 198.83, 159.54, 136.28, 128.93, 128.16, 127.78, 116.27, 44.97, 34.97, 34.83, 29.38, 27.26 ppm.

(4) Synthesis of Compound 16

Compound 13 (1.80 g, 7.47 mmol) was dissolved in ethanol (7 mL), and 10% Pd on activated charcoal (64 mg) was added thereto. The resulting solution was hydrogenated overnight at room temperature under the ambient pressure. The resulting mixture was filtered through cellite, and the solvent was removed from the filtrate using a rotary vacuum evaporator to obtain a bright brown sold (yield: 100%). $^1$H NMR (CDCl$_3$): δ 7.00 (d, J=7.6 Hz, 1H, m-H), 6.88 (dd, J=8.0, 2.0 Hz, 1H, m-H), 6.68 (d, J=8 Hz, 1H, o-H), 4.73 (s, 1H, OH), 3.58 (t, J=6.8 Hz, 2H, CH$_2$Cl), 3.22 (septet, J=6.8 Hz, 1H, iPr-CH), 2.60 (t, J=6.8 Hz, 2H, CH$_2$), 1.88-1.72 (m, 4H, —CH$_2$CH$_2$—), 1.30 (d, J=6.8 Hz, 6H, iPr-CH$_3$) ppm. $^{13}$C {$^1$H}NMR (CDCl$_3$): δ 150.67, 134.15, 133.91, 126.16, 126.08, 115.03, 45.01, 34.56, 32.21, 28.94, 27.08, 22.70 ppm.

The bright brown solid was formylated using the same procedure employed for synthesizing Compound 2 to obtain Compound 16 (yield: 64%). $^1$H NMR (CDCl$_3$): δ 11.22 (s, 1H, OH), 9.85 (s, 1H, CHO), 7.28 (d, J=1.6 Hz, 1H, m-H), 7.19 (d, J=2.4 Hz, 1H, m-H), 3.59 (t, J=6.0 Hz, 2H, CH$_2$Cl), 3.37 (septet, J=6.8 Hz, 1H, iPr-CH), 2.65 (t, J=6.8 Hz, 2H, CH$_2$), 1.88-1.77 (m, 4H, —CH$_2$CH$_2$—), 1.27 (d, J=6.8 Hz, 6H, iPr-CH$_3$) ppm. $^{13}$C {$^1$H}NMR (CDCl$_3$): δ 196.52, 157.32, 136.88, 133.88, 132.67, 130.09, 119.78, 44.87, 34.26, 32.07, 28.66, 26.38, 22.39 ppm.

(5) Synthesis of Compound 17

The procedure for synthesizing Compound 16 was repeated except that Compound 14 was used instead of compound 13 to obtain Compound 17. $^1$H NMR (CDCl$_3$): δ 6.96 (s, 1H, m-H), 6.90 (dd, J=8.0, 2.0 Hz, 1H, m-H), 6.71 (d, J=8 Hz, 1H, o-H), 4.82 (s, 1H, OH), 3.58 (t, J=6.4 Hz, 2H, —CH$_2$Cl), 2.58 (t, J=7.2 Hz, 2H, —CH$_2$), 2.27 (s, 3H, —CH$_3$), 1.87-1.72 (m, 4H, —CH$_2$CH$_2$—) ppm. $^{13}$C {$^1$H}NMR (CDCl$_3$): δ 151.61, 133.84, 130.79, 126.62, 123.41, 114.62, 45.08, 34.23, 32.11, 28.93, 15.91 ppm.

(6) Synthesis of Compound 18

The procedure for synthesizing Compound 16 was repeated except that Compound 15 was used instead of Compound 13 to obtain Compound 18. $^1$H NMR (CDCl$_3$): δ 7.08 (d, J=2.4 Hz, 1H, m-H), 6.90 (dd, J=8.0, 2.4 Hz, 1H, m-H), 6.62 (d, J=8 Hz, 1H, o-H), 5.00 (s, 1H, OH), 3.59 (t, J=6.4 Hz, 2H, —CH$_2$Cl), 2.60 (t, J=7.2 Hz, 2H, —CH$_2$), 1.90-1.72 (m, 4H, —CH$_2$CH$_2$—), 1.45 (s, 9H, —C(CH$_3$)$_3$) ppm. $^{13}$C {$^1$H}NMR (CDCl$_3$): δ 152.17, 135.72, 133.40, 126.92, 126.29, 115.25, 45.06, 34.65, 34.55, 32.27, 29.68, 28.99 ppm.

(7) Synthesis of Compound 19

The procedure for synthesizing Compound 3 was repeated except that Compound 16 was used instead of Compound 2 and the reaction was allowed to proceed for 2 days to obtain Compound 19 (yield: 98%). $^1$H NMR (CDCl$_3$): δ 11.24 (s, 1H, OH), 9.86 (s, 1H, CHO), 7.32 (d, J=2.0 Hz, 1H, m-H), 7.27 (s, J=2.4 Hz, 1H, m-H), 3.32 (septet, J=6.8 Hz, 1H, iPr-CH), 3.26-3.06 (m, 8H, —NCH$_2$), 2.67 (t, J=6.8 Hz, 2H, CH$_2$), 1.76-1.66 (m, 6H, CH$_2$) 1.62-1.52 (m, 6H, CH$_2$), 1.44-1.32 (m, 6H, CH$_2$), 1.23 (d, J=6.8 Hz, 6H, iPr-CH$_3$), 0.95 (t, J=7.6 Hz, 9H, CH$_3$) ppm. $^{13}$C {$^1$H}NMR (CDCl$_3$): δ 197.18, 157.30, 136.76, 133.81, 131.86, 130.75, 119.82, 58.37, 33.82, 27.68, 26.38, 25.59, 23.75, 22.33, 21.00, 19.90, 19.60, 13.59 ppm.

(8) Synthesis of Compound 20

The procedure for synthesizing Compound 19 was repeated except that Compound 17 was used instead of Compound 16 to obtain Compound 20. $^1$H NMR (CDCl$_3$): δ 11.13 (s, 1H, OH), 9.85 (s, 1H, CHO), 7.31 (d, J=2.0 Hz, 1H, m-H), 7.24 (s, J=2.4 Hz, 1H, m-H), 3.24-3.09 (m, 8H, —NCH$_2$), 2.66 (t, J=6.8 Hz, 2H, CH$_2$), 2.24 (S, 3H, —CH$_3$), 1.74-1.68 (m, 6H, CH$_2$) 1.61-1.53 (m, 6H, CH$_2$), 1.44-1.32 (m, 6H, CH$_2$), 0.96 (t, J=7.6 Hz, 9H, CH$_3$) ppm. $^{13}$C {$^1$H}NMR (CDCl$_3$): δ 196.99, 158.05, 138.10, 131.69, 130.84, 126.52, 119.67, 58.40, 33.48, 27.62, 23.77, 20.83, 19.89, 19.62, 15.07, 13.60 ppm.

(9) Synthesis of Compound 21

The procedure for synthesizing Compound 19 was repeated except that Compound 18 was used instead of Compound 16 to obtain Compound 21. $^1$H NMR (CDCl$_3$): δ 11.67 (s, 1H, OH), 9.86 (s, 1H, CHO), 7.34 (d, J=2.0 Hz, 1H, m-H), 7.32 (s, J=2.4 Hz, 1H, m-H), 3.23-3.08 (m, 8H, —NCH$_2$), 2.69 (t, J=6.8 Hz, 2H, CH$_2$), 1.76-1.68 (m, 6H, CH$_2$), 1.63-1.55 (m, 6H, CH$_2$), 1.41 (s, 9H, —C(CH$_3$)$_3$), 1.44-1.35 (m, 6H, CH$_2$), 0.98 (t, J=7.6 Hz, 9H, CH$_3$) ppm. $^{13}$C {$^1$H}NMR (CDCl$_3$): δ 197.42, 159.29, 137.96, 134.33, 131.30, 120.31, 58.43, 34.84, 33.95, 29.29, 27.71, 23.80, 21.09, 19.91, 19.64, 13.62 ppm.

(10) Synthesis of Compound 22

The procedure for synthesizing Compound 4 was repeated except that Compound 19 was used instead of Compound 3 to obtain Compound 22. $^1$H NMR (CDCl$_3$): δ 8.24 (s, 1H, CHO), 7.02 (d, J=1.6 Hz, 1H, m-H), 6.80 (s, J=1.6 Hz, 1H, m-H), 3.32 (septet, J=6.8 Hz, 1H, iPr-CH), 3.06-3.20 (m, 8H, NCH$_2$), 2.55 (t, J=6.8 Hz, 2H, CH$_2$), 2.02-1.92 (m, 2H, cyclohexyl-CH$_2$), 1.90-1.84 (m, 2H, cyclohexyl-CH$_2$), 1.66-1.56 (m, 6H, butyl-CH$_2$) 1.55-1.44 (m, 6H, butyl-CH$_2$), 1.39-1.27 (m, 4H, CH$_2$), 1.23 (d, J=5.2 Hz, 3H, iPr-CH$_3$), 1.21 (d, J=5.2 Hz, 3H, iPr-CH$_3$), 0.90 (t, J=7.6 Hz, 9H, butyl-CH$_3$) ppm. $^{13}$C {$^1$H}NMR (CDCl$_3$): δ 164.91, 156.53, 135.77, 130.28, 128.81, 128.39, 117.67, 72.18, 58.31, 33.99, 32.96, 27.85, 26.51, 24.15, 23.68, 22.65, 22.52, 20.99, 19.55, 13.61, 13.55 ppm.

(11) Synthesis of Compound 23

The procedure for synthesizing Compound 22 was repeated except that Compound 20 was used instead of Compound 19 to obtain Compound 23. $^1$H NMR (CDCl$_3$): δ 8.20 (s, 1H, CHO), 6.96 (d, J=1.6 Hz, 1H, m-H), 6.79 (s, J=1.6 Hz, 1H, m-H), 3.31-3.28 (m, 1H, cyclohexyl-CH), 3.10-3.06 (m, 8H, NCH$_2$), 2.52 (t, J=6.8 Hz, 2H, CH$_2$), 2.18 (s, 3H, —CH$_3$), 1.93-1.90 (m, 2H, cyclohexyl-CH$_2$), 1.87-1.84 (m, 2H, cyclohexyl-CH$_2$), 1.73-1.50 (m, 16H, —CH$_2$), 1.35-1.26 (m, 8H, —CH$_2$), 0.88 (t, J=7.6 Hz, 9H, butyl-CH$_3$) ppm. $^{13}$C {$^1$H}NMR (CDCl$_3$): δ 164.52, 157.38, 133.26, 130.15, 128.51, 125.36, 117.52, 72.38, 58.30, 33.58, 33.10, 27.80, 24.15, 23.67, 20.75, 19.89, 19.54, 15.55, 13.55 ppm.

(12) Synthesis of Compound 24

The procedure for synthesizing Compound 22 was repeated except that Compound 21 was used instead of Compound 19 to obtain Compound 24. $^1$H NMR (CDCl$_3$): δ 8.23 (s, 1H, CHO), 7.04 (d, J=1.6 Hz, 1H, m-H), 6.79 (s, J=1.6 Hz, 1H, m-H), 3.33-3.31 (m, 1H, cyclohexyl-CH), 3.14-3.07 (m, 8H, NCH$_2$), 2.53 (t, J=6.8 Hz, 2H, CH$_2$), 2.00-1.97 (m, 2H, cyclohexyl-CH$_2$), 1.89-1.86 (m, 2H, cyclohexyl-CH$_2$), 1.70-1.49 (m, 16H, —CH$_2$), 1.40 (s, 9H, —C(CH$_3$)$_3$), 1.38-1.29 (m, 8H, —CH$_2$), 0.90 (t, J=7.6 Hz, 9H, butyl-CH$_3$) ppm. $^{13}$C {$^1$H}NMR (CDCl$_3$): δ 165.25, 158.32, 136.76, 129.56, 129.22, 128.97, 118.19, 71.97, 58.27, 34.72, 34.06, 32.94, 29.46, 27.81, 24.22, 23.66, 21.00, 19.88, 19.53, 13.52 ppm.

(13) Synthesis of Compound 25

The procedure for synthesizing Compound 5 was repeated except that Compound 22 was used instead of Compound 4 to obtain Compound 25. $^1$H NMR (dmso-d$_6$): δ 8.58 (d, J=0.8 Hz, 3H, (NO$_2$)$_2$C$_6$H$_3$O), 7.90 (s, 2H, CH=N), 7.75 (dd, J=9.6, 3.2 Hz, 3H, (NO$_2$)$_2$C$_6$H$_3$O), 7.68 (s, 2H, m-H), 7.45 (s, 2H, m-H), 6.30 (d, J=9.6, 3H, (NO$_2$)$_2$C$_6$H$_3$O), 3.63-3.57 (br, 2H, cyclohexyl-CH) 3.23-3.12 (m, 12H, NCH$_2$), 3.12-3.02 (m, 4H, NCH$_2$), 2.08-1.96 (br, 4H, cyclohexyl-CH$_2$), 1.96-1.82 (br, 4H, cyclohexyl-CH$_2$), 1.74 (s, 18H, CH$_3$), 1.70-1.52 (m, 12H, butyl-CH$_2$), 1.36-1.25 (m, 12H, butyl-CH$_2$), 0.92 (t, J=7.6 Hz, 18H, CH$_3$), 0.71 (t, J=8.0, 4H, SiCH$_2$), 0.30 (s, 3H, SiCH$_3$), 0.29 (s, 3H, SiCH$_3$) ppm. $^{13}$C {$^1$H}NMR (dmso-d$_6$): δ 168.42, 164.14, 161.48, 141.76, 136.85, 131.84, 131.67, 131.47, 131.12, 129.94, 128.38, 127.88, 125.81, 125.05, 118.74, 70.12, 58.38, 55.68, 34.22, 30.18, 28.78, 25.12, 24.32, 23.93, 23.48, 21.67, 20.08, 14.34 ppm.

(14) Synthesis of Compound 26

The procedure for synthesizing Compound 25 was repeated except that Compound 23 was used instead of Compound 22 to obtain Compound 26. $^1$H NMR (dmso-d$_6$): δ 8.61 (br, 3H, (NO$_2$)$_2$C$_6$H$_3$O), 7.88 (br, 5H, (NO$_2$)$_2$C$_6$H$_3$O and CH=N), 7.25 (s, 2H, m-H), 7.17 (s, 2H, m-H), 6.49 (d, J=9.6, 3H, (NO$_2$)$_2$C$_6$H$_3$O), 4.02 (br, 2H, iPr-), 3.59 (br, 2H, cyclohexyl-CH). 3.36-3.10 (br, 16H, —NCH$_2$), 2.59 (br, 4H, —CH$_2$), 2.08-1.96 (br, 4H, cyclohexyl-CH$_2$), 1.92-1.78 (br, 4H, cyclohexyl-CH$_2$), 1.70-1.50 (m, 16H, —CH$_2$), 1.48-1.38 (br, 12H, iPr-CH$_3$), 1.34-1.22 (m, 16H, —CH$_2$), 0.92 (t, J=6.8 Hz, 18H, CH$_3$) ppm. $^{13}$C {$^1$H}NMR (dmso-d$_6$): δ 168.42, 164.14, 161.48, 141.76, 136.85, 131.84, 131.67, 131.47, 131.12, 129.94, 128.38, 127.88, 125.81, 125.05, 118.74, 70.12, 58.38, 55.68, 34.22, 30.18, 28.78, 25.12, 24.32, 23.93, 23.48, 21.67, 20.08, 14.34 ppm.

(15) Synthesis of Compound 27

The procedure for synthesizing Compound 25 was repeated except that Compound 24 was used instead of Compound 22 to obtain Compound 27. $^1$H NMR (dmso-d$_6$): δ 8.75 (br, 3H, (NO$_2$)$_2$C$_6$H$_3$O), 7.94 (br, 3H, (NO$_2$)$_2$C$_6$H$_3$O), 7.74 (s, 2H, CH=N), 7.28 (s, 2H, m-H), 7.21 (s, 2H, m-H), 6.45 (d, J=9.6, 3H, (NO$_2$)$_2$C$_6$H$_3$O), 3.58 (br, 2H, cyclohexyl-CH). 3.28-3.14 (br, 16H, —NCH$_2$), 3.03-3.00 (m, 4H, —CH$_2$), 2.60 (br, 4H, —CH$_2$), 2.06-1.94 (br, 4H, cyclohexyl-CH$_2$), 1.90-1.82 (br, 4H, cyclohexyl-CH$_2$), 1.71 (s, 18H, —C(CH$_3$)$_3$), 1.66-1.50 (m, 28H, —CH$_2$), 1.36-1.26 (m, 16H, —CH$_2$), 0.91 (t, J=6.8 Hz, 18H, CH$_3$) ppm.

Example 5

Preparation of the complex of formula (6e)

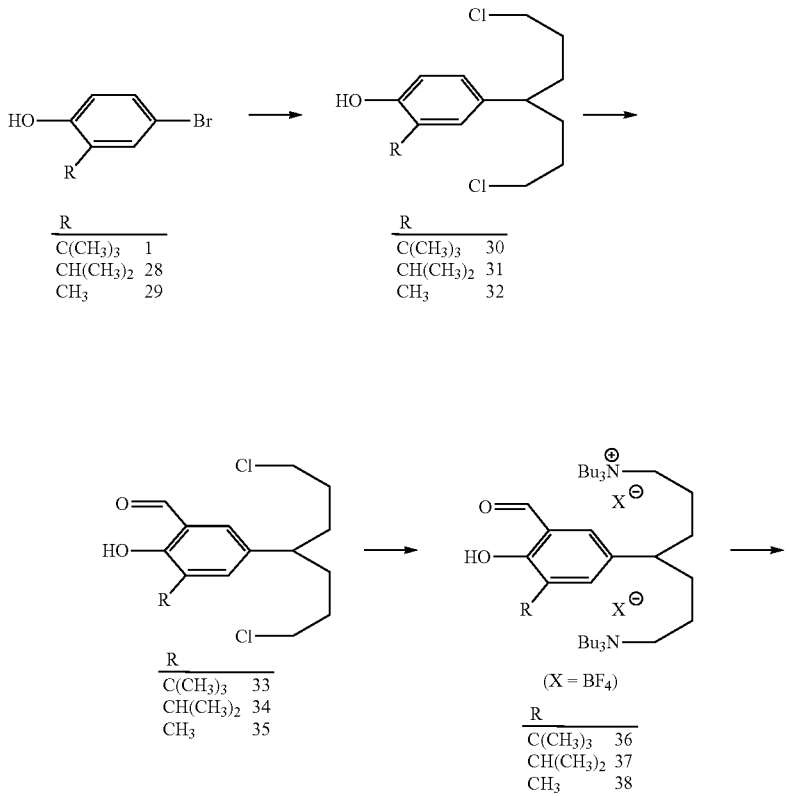

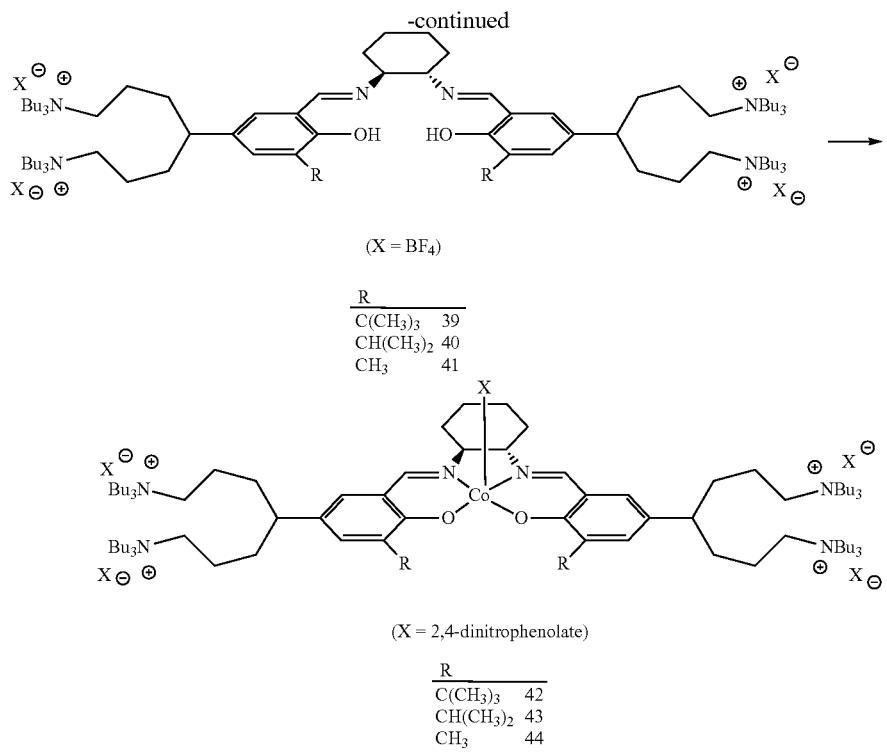

(X = BF$_4$)

| R | |
|---|---|
| C(CH$_3$)$_3$ | 39 |
| CH(CH$_3$)$_2$ | 40 |
| CH$_3$ | 41 |

(X = 2,4-dinitrophenolate)

| R | |
|---|---|
| C(CH$_3$)$_3$ | 42 |
| CH(CH$_3$)$_2$ | 43 |
| CH$_3$ | 44 |

(1) Synthesis of Compound 30

4-Bromo-2-tert-butylphenol (1.00 g, 4.37 mmol) was dissolved in THF (50 mL) under a nitrogen atmosphere, tert-BuLi (1.7 M in pentane 5.86 g, 15.28 mmol) was added thereto at −78° C. using a syringe. The reaction was allowed to proceed while stirring at −78° C. for 2 hours. 1,7-Dichloroheptane-4-one (0.96 g, 5.24 mmol) and LiCl (0.22 g, 5.24 mmol) were added to the reaction mixture while stirring −78° C. over 2 hours. After the solution was stirred for 2 hours at −78° C., aqueous saturated NH$_4$Cl solution (15 mL) was added to quench the reaction. The product was extracted using diethyl ether (3×15 mL). After the combined organic phase was dried over anhydrous MgSO$_4$, the solvent was removed with rotary evaporator to give an oily residue. The major side product of the reaction was 2-tert-butyl phenol, generated by the protonation of the lithiated compound. It was not easy to remove the side product from the hydrogenated product by column chromatography. Therefore, the side product was eliminated by the following procedure: the oily residue was transferred into a separatory funnel, and then diethyl ether (10 mL) and aqueous KOH solution (22 w %, 5 mL) were added. The mixture was vigorously shaken to give three phases. The upper layer was diethyl ether phase. The middle layer was a potassium phenolate of the desired products. The bottom layer was an aqueous phase containing potassium 2-tert-butylphenolate. After the bottom layer was discarded, aqueous saturated NH$_4$Cl solution (5 mL) was added. By the addition, the phenolate anion of the desired products was protonated to be soluble in the diethyl ether phase. The ether phase was collected and dried over anhydrous MgSO$_4$. The solvent was removed with a rotary evaporator to give an oily residue which was purified by column chromatography. The benzylic tertiary alcohol was obtained by eluting hexane and ethyl acetate (v/v, 2:1). The obtained compound was then dissolved in ethanol (5 mL). Pd on activated charcoal (10 w %) was added, and then the solution was stirred overnight at room temperature under an atmospheric pressure of H$_2$ gas. The solution was filtered over Celite, and then solvent was removed with a rotary evaporator to give a residue, which was purified by column chromatography on silica gel eluting with hexane and ethyl acetate (v/v, 2:1) to obtain Compound 30 (yield: 83%). $^1$H NMR (CDCl$_3$): δ 7.02 (d, J=2.0 Hz, 1H, m-H), 6.84 (dd, J=8.0, 2.0 Hz, 1H, m-H), 6.62 (d, J=8.0 Hz, 1H, o-H), 4.93 (s, 1H, OH), 3.49 (t, J=5.6 Hz, 4H, —CH$_2$Cl), 2.49 (quintet, J=4.8 Hz, 1H, —CH—), 1.88-1.75 (m, 4H, CH$_2$), 1.72-1.61 (m, 4H, CH$_2$), 1.45 (s, 9H, —C(CH$_3$)$_3$) ppm. $^{13}$C {$^1$H}NMR (CDCl$_3$): δ 152.36, 135.86, 135.82, 126.02, 125.21, 115.38, 45.26, 44.34, 34.56, 34.14, 30.66, 29.71 ppm (2) Synthesis of Compound 31

The procedure for synthesizing Compound 30 was repeated except that 4-bromo-2-isobutylphenol was used instead of 4-bromo-2-tert-butylphenol to obtain Compound 31. $^1$H NMR (CDCl$_3$): δ 6.94 (d, J=2.0 Hz, 1H, m-H), 6.83 (dd, J=8.0, 2.0 Hz, 1H, m-H), 6.69 (d, J=8.0 Hz, 1H, o-H), 4.73 (s, 1H, OH), 3.48 (t, J=5.6 Hz, 4H, —CH$_2$Cl), 3.21 (septet, J=6.8 Hz, 1H, iPr-CH), 2.48 (quintet, J=4.8 Hz, 1H, —CH—), 1.82-1.60 (m, 8H, —CH$_2$), 1.28 (d, J=6.8 Hz, 6H, iPr-CH$_3$) ppm. $^{13}$C {$^1$H}NMR (CDCl$_3$): δ 150.86, 136.39, 134.21, 125.30, 125.12, 115.16, 45.27, 44.34, 34.17, 30.66, 27.17, 22.71 ppm.

(3) Synthesis of Compound 32

The procedure for synthesizing Compound 30 was repeated except that 4-bromo-2-methylphenol was used instead of 4-bromo-2-tert-butylphenol to obtain Compound 32. During the work up procedure, benzylic tert-alcohol along with its H$_2$O eliminated, corresponding alkene also observed. The H$_2$O eliminated alkene product was obtained from the column by eluting with hexane and ethyl acetate (v/v, 10:1), and the benzylic tert-alcohol was obtained by eluting the column with hexane and ethyl acetate (v/v, 2:1). Both the compounds were combined for the reduction procedure. $^1$H NMR (CDCl$_3$): δ 6.88 (d, J=2.0 Hz, 1H, m-H), 6.82 (dd, J=8.0, 2.0 Hz, 1H, m-H), 6.72 (d, J=8.0 Hz, 1H, o-H), 4.70 (s, 1H, OH), 3.49 (t, J=5.6 Hz, 4H, —CH$_2$Cl), 2.46 (quintet, J=4.8 Hz, 1H, —CH—), 2.28 (s, 3H, —CH$_3$), 1.82-1.60 (m, 8H, —CH$_2$) ppm.

(4) Synthesis of Compound 33

The procedure for synthesizing Compound 2 was repeated except that Compound 30 was used instead of Compound 1 to obtain Compound 33 (yield: 84%). $^1$H NMR (CDCl$_3$): δ11.67 (s, 1H, OH), 9.85 (s, 1H, CHO), 7.30 (d, J=2.4 Hz, 1H, m-H), 7.16 (d, J=2.4 Hz, 1H, m-H), 3.49 (t, J=5.6 Hz, 4H, —CH$_2$Cl), 2.56 (quintet, J=5.2 Hz, 1H, —CH—), 1.88-1.81 (m, 2H, —CH$_2$), 1.76-1.59 (m, 6H, —CH$_2$—), 1.44 (s, 9H, —C(CH$_3$)$_3$) ppm. $^{13}$C {$^1$H}NMR (CDCl$_3$): δ 196.74, 159.50, 138.29, 134.59, 133.17, 129.91, 120.25, 45.02, 44.19, 34.91, 33.85, 30.51, 29.28 ppm.

(5) Synthesis of Compound 34

The procedure for synthesizing Compound 33 was repeated except that Compound 31 was used instead of Compound 30 to obtain Compound 34. $^1$H NMR (CDCl$_3$): δ 11.27 (s, 1H, OH), 9.86 (s, 1H, CHO), 7.28 (d, J=2.4 Hz, 1H, m-H), 7.12 (d, J=2.4 Hz, 1H, m-H), 3.47 (t, J=5.6 Hz, 4H, —CH$_2$Cl), 3.33 (septet, J=6.8 Hz, 1H, iPr-CH), 2.58 (quintet, J=5.2 Hz, 1H, —CH—), 1.86-1.78 (m, 2H, —CH$_2$), 1.76-1.56 (m, 6H, —CH$_2$—), 1.26 (d, J=6.8 Hz, 6H, -iPr-CH$_3$) ppm.

(6) Synthesis of Compound 35

The procedure for synthesizing Compound 33 was repeated except that Compound 32 was used instead of Compound 30 to obtain Compound 35. $^1$H NMR (CDCl$_3$): δ 11.18 (s, 1H, OH), 9.82 (s, 1H, CHO), 7.22 (d, J=2.4 Hz, 1H, m-H), 7.14 (d, J=2.4 Hz, 1H, m-H), 3.49 (t, J=5.6 Hz, 4H, —CH$_2$Cl), 2.54 (quintet, J=5.2 Hz, 1H, —CH—), 2.30 (s, 3H, —CH$_3$), 1.88-1.81 (m, 2H, —CH$_2$), 1.76-1.59 (m, 6H, —CH$_2$—) ppm.

(7) Synthesis of Compound 36

The procedure for synthesizing Compound 3 was repeated except that Compound 33 was used instead of Compound 2 and the crude product was purified by column chromatography (ethanol:methylene chloride=1:20) to obtain Compound 36 (yield: 35%). $^1$H NMR (CDCl$_3$): δ 11.76 (s, 1H, OH), 9.92 (s, 1H, CHO), 7.53 (s, 1H, m-H), 7.35 (s, 1H, m-H), 3.36-3.22 (m, 16H, —NCH$_2$), 2.82 (br, 1H, —CH—), 1.78-1.70 (m, 4H, —CH$_2$), 1.66-1.46 (m, 16H, —CH$_2$), 1.42 (s, 9H, —C(CH$_3$)$_3$), 1.38-1.32 (m, 12H, butyl-CH$_2$), 0.93 (t, J=7.6 Hz, 18H, CH$_3$) ppm. $^{13}$C {$^1$H}NMR (CDCl$_3$): δ 197.76, 159.67, 138.70, 133.50, 132.63, 131.10, 120.40, 58.55, 41.45, 34.99, 32.28, 29.31, 23.72, 19.59, 19.00, 13.54 ppm.

(8) Synthesis of Compound 37

The procedure for synthesizing Compound 36 was repeated except that Compound 34 was used instead of Compound 33 to obtain Compound 37. $^1$H NMR (CDCl$_3$): δ 11.27 (s, 1H, OH), 9.86 (s, 1H, CHO), 7.28 (d, J=2.4 Hz, 1H, m-H), 7.12 (d, J=2.4 Hz, 1H, m-H), 3.47 (t, J=5.6 Hz, 4H, —CH$_2$Cl), 3.33 (septet, J=6.8 Hz, 1H, iPr-CH), 2.58 (quintet, J=5.2 Hz, 1H, —CH—), 1.86-1.78 (m, 2H, —CH$_2$), 1.76-1.56 (m, 6H, —CH$_2$—), 1.26 (d, J=6.8 Hz, 6H, -iPr-CH$_3$) ppm.

(9) Synthesis of Compound 38

The procedure for synthesizing Compound 36 was repeated except that Compound 35 was used instead of Compound 33 to obtain Compound 38. $^1$H NMR (CDCl$_3$): δ 11.19 (s, 1H, OH), 9.89 (s, 1H, CHO), 7.48 (s, 1H, m-H), 7.29 (s, 1H, m-H), 3.32-3.26 (m, 4H, —NCH$_2$), 3.10-3.06 (m, 12H, —NCH$_2$), 2.77 (septet, J=6.8 Hz, 1H, —CH—), 2.24 (s, 3H, —CH$_3$), 1.76-1.64 (m, 8H, —CH$_2$), 1.58-1.44 (m, 16H, —CH$_2$), 1.34-1.29 (m, 8H, —CH$_2$), 0.90 (t, J=7.6 Hz, 18H, CH$_3$) ppm.

(10) Synthesis of Compound 39

The procedure for synthesizing Compound 4 was repeated except that Compound 36 was used instead of Compound 3 and the crude product was purified by column chromatography (ethanol:methylene chloride=1:20) to obtain Compound 39 (yield: 85%). $^1$H NMR (CDCl$_3$): δ 8.37 (s, 1H, CHO), 7.00 (s, 2H, m-H), 3.44-3.38 (m, 1H, cyclohexyl-CH), 3.32-2.98 (m, 16H, —NCH$_2$), 2.63 (br, 1H, —CH—), 1.94-1.82 (m, 2H, cyclohexyl-CH$_2$), 1.78-1.70 (m, 2H, cyclohexyl-CH$_2$), 1.68-1.58 (m, 4H, —CH$_2$—), 1.66-1.42 (m, 16H, —CH$_2$), 1.38 (s, 9H, —C(CH$_3$)$_3$), 1.34-1.21 (m, 12H, butyl-CH$_2$), 0.91 (t, J=7.2 Hz, 9H, butyl-CH$_3$), 0.80 (t, J=7.2 Hz, 9H, butyl-CH$_3$) ppm. $^{13}$C {$^1$H}NMR (CDCl$_3$): δ 164.79, 159.11, 137.71, 131.14, 128.78, 127.38, 118.48, 71.96, 58.14, 57.93, 41.25, 34.89, 33.48, 33.20, 32.54, 29.39, 24.22, 23.59, 23.48, 19.53, 19.38, 18.94, 13.51, 13.33 ppm.

(11) Synthesis of Compound 40

The procedure for synthesizing Compound 39 was repeated except that Compound 37 was used instead of Compound 36 to obtain Compound 40. $^1$H NMR (CDCl$_3$): δ 8.41 (s, 1H, CHO), 7.04 (s, 2H, m-H), 3.49-3.40 (m, 1H, cyclohexyl-CH), 3.31 (septet, J=6.8 Hz, 1H, iPr-CH), 3.18-2.98 (m, 16H, —NCH$_2$), 2.68 (br, 1H, —CH—), 1.92-1.82 (m, 2H, cyclohexyl-CH$_2$), 1.78-1.70 (m, 2H, cyclohexyl-CH$_2$), 1.68-1.58 (m, 16H, —CH$_2$—), 1.66-1.42 (m, 16H, —CH$_2$), 1.40-1.32 (m, 6H, butyl-CH$_2$), 1.30-1.18 (m, 12H. —CH$_2$ and iPr-CH$_3$), 0.94 (t, J=7.2 Hz, 9H, butyl-CH$_3$), 0.84 (t, J=7.2 Hz, 9H, butyl-CH$_3$) ppm.

(12) Synthesis of Compound 41

The procedure for synthesizing Compound 39 was repeated except that Compound 38 was used instead of Compound 36 to obtain Compound 41. $^1$H NMR (CDCl$_3$): δ 8.37 (s, 1H, CHO), 7.02 (s, 2H, m-H), 3.43-3.41 (m, 1H, cyclohexyl-CH), 3.36-3.28 (m, 4H, —NCH$_2$), 3.18-3.05 (m, 12H, —NCH$_2$), 2.68 (br, 1H, —CH—), 2.23 (s, 3H, —CH$_3$), 1.94-1.82 (m, 4H, cyclohexyl-CH$_2$), 1.78-1.60 (m, 8H, —CH$_2$), 1.58-1.40 (m, 16H, —CH$_2$), 1.38-1.25 (m, 8H, —CH$_2$), 0.92 (t, J=7.2 Hz, 9H, butyl-CH$_3$), 0.86 (t, J=7.2 Hz, 9H, butyl-CH$_3$) ppm.

(13) Synthesis of Compound 42

The procedure for synthesizing Compound 5 was repeated except that Compound 39 was used instead of Compound 4 to obtain Compound 42. $^1$H NMR (dmso-d$_6$): δ 8.67 (br, 5H, (NO$_2$)$_2$C$_6$H$_3$O), 7.82 (br, 5H, (NO$_2$)$_2$C$_6$H$_3$O), 7.72 (s, 2H, CH=N), 7.34 (s, 2H, m-H), 7.19 (s, 2H, m-H), 6.36 (br, 5H, (NO$_2$)$_2$C$_6$H$_3$O), 3.57-3.50 (br, 2H, cyclohexyl-CH), 3.28-2.84 (m, 32H, —NCH$_2$), 2.60-2.52 (br, 2H, —CH), 1.06-1.96 (br, 4H, cyclohexyl-CH$_2$), 1.90-1.78 (br, 4H, cyclohexyl-CH$_2$), 1.70 (s, 18H, —C(CH$_3$)$_3$), 1.62-1.38 (br, 48H, butyl-CH$_2$), 1.32-1.50 (m, 16H, —CH$_2$), 0.85 (t, J=7.2 Hz, 36H, CH$_3$ ppm. $^{13}$C {$^1$H}NMR (dmso-d$_6$): δ 164.01, 162.91, 143.19, 132.15, 130.85, 129.51, 128.59, 128.01 (br), 125.79 (br), 119.56, 69.71, 58.37, 58.14, 56.37, 42.94, 36.28, 33.56, 31.03, 30.13, 24.95, 23.66, 19.85, 14.12 ppm.

(14) Synthesis of Compound 43

The procedure for synthesizing Compound 42 was repeated except that Compound 40 was used instead of Compound 39 to obtain Compound 43. $^1$H NMR (dmso-d$_6$): δ 8.61 (br, 5H, (NO$_2$)$_2$C$_6$H$_3$O), 7.86 (s, 2H, CH=N), 7.81 (br, 5H, (NO$_2$)$_2$C$_6$H$_3$O), 7.31 (s, 2H, m-H), 7.17 (s, 2H, m-H), 6.36 (br, 5H, (NO$_2$)$_2$C$_6$H$_3$O), 4.02-3.62 (br, 2H, iPr-CH$_3$), 3.57-3.48 (br, 2H, cyclohexyl-CH), 3.29-2.90 (m, 32H, —NCH$_2$), 2.08-1.98 (br, 4H, cyclohexyl-CH$_2$), 1.87-1.74 (br, 4H, cyclohexyl-CH$_2$), 1.66-1.34 (br, 52H, —CH$_2$), 1.29-1.12 (m, 36H, —CH$_2$), 0.89 (br, 36H, butyl-CH$_3$) ppm.

(15) Synthesis of Compound 44

The procedure for synthesizing Compound 42 was repeated except that Compound 41 was used instead of Compound 39. $^1$H NMR (dmso-d$_6$): δ 8.62 (br, 5H, (NO$_2$)$_2$C$_6$H$_3$O), 7.70 (br, 7H, (NO$_2$)$_2$C$_6$H$_3$O and CH=N), 7.33 (s, 2H, m-H), 7.21 (s, 2H, m-H), 6.33 (br, 5H, (NO$_2$)$_2$C$_6$H$_3$O), 3.56-3.50 (br, 2H, cyclohexyl-CH), 3.30-2.87 (m, 32H, —NCH$_2$), 2.61 (s, 6H, —CH$_3$), 2.08-1.96 (br, 4H, cyclohexyl-CH$_2$), 1.88-1.76 (br, 4H, cyclohexyl-CH$_2$), 1.66-1.32 (br, 52H, —CH$_2$), 1.29-1.10 (m, 36H, —CH$_2$), 0.84 (br, 36H, butyl-CH$_3$) ppm.

Example 6

Preparation of the complex of formula (6f)

Synthesis of Compound 45

Compound 4 (0.050 g, 0.043 mmol) and CrCl$_2$ (0.005 g, 0.043 mmol) were dissolved in tetrahydrofuran (2 mL) under a nitrogen atmosphere, and the reaction was allowed to proceed overnight while stirring at room temperature. The resulting solution was exposed to air, trichloroacetic acid was added thereto, and stirred for a day. Sodium trichloroacetate was added to the reaction mixture, and stirred for 3 hours. The resulting solution was filtered through cellite, and the solvent was removed from the filtrate. The residue was dissolved in methylene chloride, and the resulting solution was filtered. The solvent was removed from the filtrate to obtain Compound 45 as a bright brown solid.

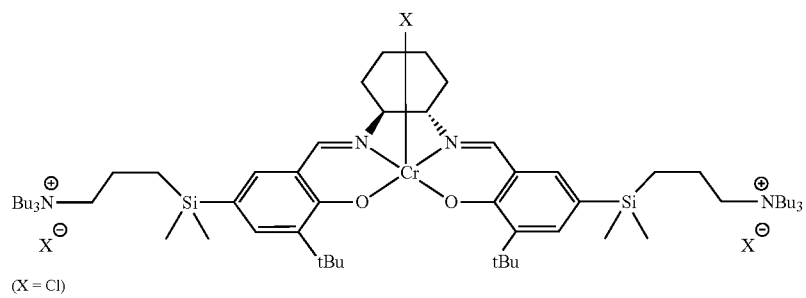

45

(X = Cl)

Examples 7 to 22

Copolymerization of Polycarbonates

Using the catalyst specified in Table 1, each of the compound prepared in Examples and propylene oxide (10.0 g, 172 mmol) were placed in a 50 mL bomb reactor and the reactor was sealed. The reactor was immersed in an oil bath having a set temperature and the reactants in the reactor were stirred under a carbon dioxide partial pressure of 20 bar. With the progress of the reaction, the carbon dioxide pressure dropped, and when the carbon dioxide pressure dropped by about 3 bar, the reaction was terminated by venting carbon dioxide. The resulting viscous liquid was added dropwise to methanol and stirred for 12 hours to induce the formation of a polymer as a white solid. The resultant polymer was isolated and dried in a vacuum at 60° C. The results are shown in Table 1.

Comparative Examples 1 to 5

To compare the reactivities of the inventive catalysts with that of the known catalysts, copolymerization was performed as described in Example 7 except that Compounds 46 and 47 were used as comparative catalysts.

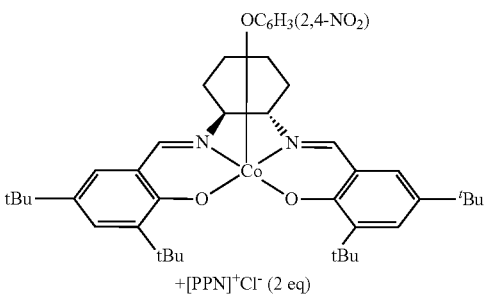

46

+[PPN]$^+$Cl$^-$ (2 eq)

-continued

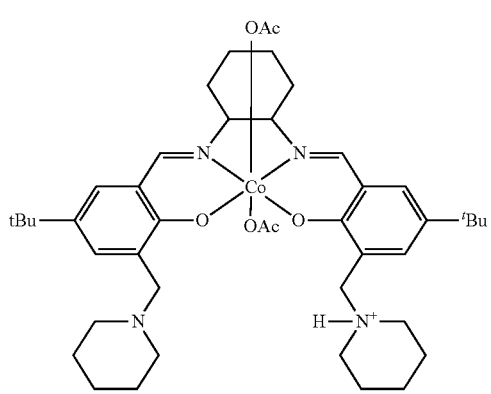

47

The comparative catalyst Compound 46 exhibited a TOF value of 1,400 h$^{-1}$ under the conditions of [propylene oxide]/[catalyst] ratio of 2,000 and the temperature of 45° C. (see Comparative Example 2), but do not provide any copolymer at the temperature of 80° C. and at [propylene oxide]/[catalyst] ratio of 25,000 (see Comparative Example 1).

A catalyst system of Compound 47 having tertiary ammonium salt has recently been reported [K. Nakano, T. Kamada, K. Nozaki, *Angew. Chem.* 2006, 118, 7432; *Angew. Chem. Int. Ed.* 2006, 45, 7274.]. Although Compound 47 showed a high selectivity of 90% at 60° C. the selectivity decreased with the increase of the reaction temperature or the [propylene oxide]/[catalyst] ratio (see Comparative Examples 3 to 5). Furthermore, the TOF value of Compound 47 at a high [propylene oxide]/[catalyst] ratio (about 300 h$^{-1}$) was remarkably smaller than that of the inventive compound 44 (about 22,000 h$^{-1}$).

TABLE 1

Copolymerization results[a]

| Ex. No. | Comp. no. | [PO]/[Catalyst] | Temp (° C.) | TOF[b] | TON[b] | Selectivity[c] (%) | $M_n$[d] | $M_w/M_n$[d] |
|---|---|---|---|---|---|---|---|---|
| 7 | 5 | 25000 | 50 | 650 | 4600 | 100 | 75000 | 1.23 |
| 8 | 5 | 25000 | 70 | 2400 | 2400 | 94 | 61000 | 1.19 |
| 9 | 5 | 25000 | 80 | 3300 | 3300 | 94 | 71000 | 1.25 |
| 10 | 5 | 25000 | 90 | 3500 | 3500 | 90 | 80000 | 1.32 |
| 11 | 5 | 50000 | 80 | 3200 | 14500 | 84 | 53000 | 1.35 |
| 12 | 7 | 25000 | 80 | 1500 | 3000 | 89 | 44000 | 1.58 |
| 13 | 25 | 25000 | 80 | 3100 | 3100 | 95 | 11000 | 1.49 |
| 14 | 26 | 25000 | 80 | 3000 | 3000 | 89 | 36000 | 1.52 |
| 15 | 27 | 25000 | 80 | 270 | 1600 | 70 | 42000 | 1.20 |
| 16 | 42 | 25000 | 80 | 1300 | 2500 | 84 | 38000 | 1.34 |
| 17 | 43 | 25000 | 80 | 7900 | 5300 | >99 | 76000 | 1.32 |
| 18 | 44 | 25000 | 80 | 26000 | 6400 | >99 | 114000 | 1.29 |
| 19 | 44 | 50000 | 80 | 26000 | 13000 | >99 | 208000 | 1.20 |
| 20 | 44 | 100000 | 80 | 22000 | 22000 | >99 | 285000 | 1.18 |
| 21 | 44 | 150000 | 80 | 12400 | 31000 | 96 | 175000 | 1.20 |
| 22 | 45 | 10000 | 80 | 1300 | 2700 | 80 | | |
| Com. Ex. 1[e] | 46 | 25000 | 80 | 0 | 0 | 0 | | |
| Com. Ex. 2[f] | 46 | 2000 | 45 | 1400 | 980 | 97 | 26000 | 1.01 |
| Com. Ex. 3 | 47 | 25000 | 60 | 360 | 1800[g] | 76 | n.d. | n.d.[g] |
| Com. Ex. 4 | 47 | 25000 | 80 | 370 | 1100[g] | 60 | n.d. | n.d.[g] |
| Com. Ex. 5 | 47 | 2000 | 60 | 610 | 610 | 90 | 7000 | 1.22 |

[PO]/[Catalyst]: molar ratio of propylene oxide to catalyst.
[a]Polymerization conditions: propylene oxide (10.0 g, 172 mmol), CO$_2$ (initial pressure, 2.0 MPa).
TON[b]: turnover number, i.e., the number of molecules that one mole of catalyst can convert before becoming inactivated
TOF[b]: turnover frequency, i.e., turnover number per unit time.
These values are based on the weight of the resulting polymer which does not include the amount of the side product, cyclic carbonate. TON and TOF are calculated as below:
TON = the weight of the resulting polymer (g)/[102*the mol of consumed catalyst];
TOF = TON/[hours (h)].
[c]Selectivity was calculated by $^1$H NMR spectroscopy analysis of the resulting polymer solution.
[d]The molecular weight and the molecular weight distribution measured by GPC, calibrating with polystyrene having a single distribution of molecular weight as the standard material.
[e]Only cyclic carbonate was obtained at TOF of 1950 h$^{-1}$.
[f]Polymerization data reported in the literature [X.-B. Lu, L. Shi, Y.-M. Wang, R. Zhang, Y.-J. Zhang, X.-J. Peng, Z.-C. Zhang, B. Li, *J. Am. Chem. Soc.* 2006, 128, 1664].
[g]Since only a low molecular weight oligomer was obtained, the molecular weight of polymer was not measured, and, thus, TON and TOF were calculated by $^1$H NMR spectroscopy analysis of the resulting solution.
[h]Polymerization data reported in the literature [K. Nakano, T. Kamada, K. Nozaki, *Angew. Chem.* 2006, 118, 7432; *Angew. Chem. Int. Ed.* 2006, 45, 7274.].

As shown in Table 1, Compound 44 showed a high copolymerization activity at a high ratio of 100,000 of the [propylene oxide]/[catalyst] ratio and even at a high temperature of 80° C. (see example 20). Compound 44 was capable of producing the copolymer with such a high TON and TOF values as 22,000 and 22,000 h$^{-1}$ even under the condition of [propylene oxide]/[catalyst] ratio of 100,000.

Compound 44 showed a high selectivity of >99% at a high temperature and a high [propylene oxide]/[catalyst] ratio, in addition to high TOF and TON values.

Using the inventive catalyst, a high molecular weight polymer was obtained. As high molecular weight as $M_n$ is 285,000 is achieved using the inventive catalyst. The molecular weights of the polymers produced by using Compound 46 were less than 30,000. In addition, when Compound 47 was used as a catalyst, only a low molecular weight oligomer was obtained.

Examples 23 to 33

Recovering of Catalyst

Example 23

Step 1

7.0 mg of Compound 44 prepared in Example 5 and propylene oxide (9.0 g, 150 mmol) were placed in a 50 mL bomb reactor and the reactor was sealed. The reactor was immersed in an oil bath having a set temperature of 80° C., the reactants in the reactor were stirred for 15 minutes. The reaction was allowed to proceed for 30 minutes under a carbon dioxide partial pressure of 20 bar. The reaction was terminated by venting carbon dioxide.

Figure 4:
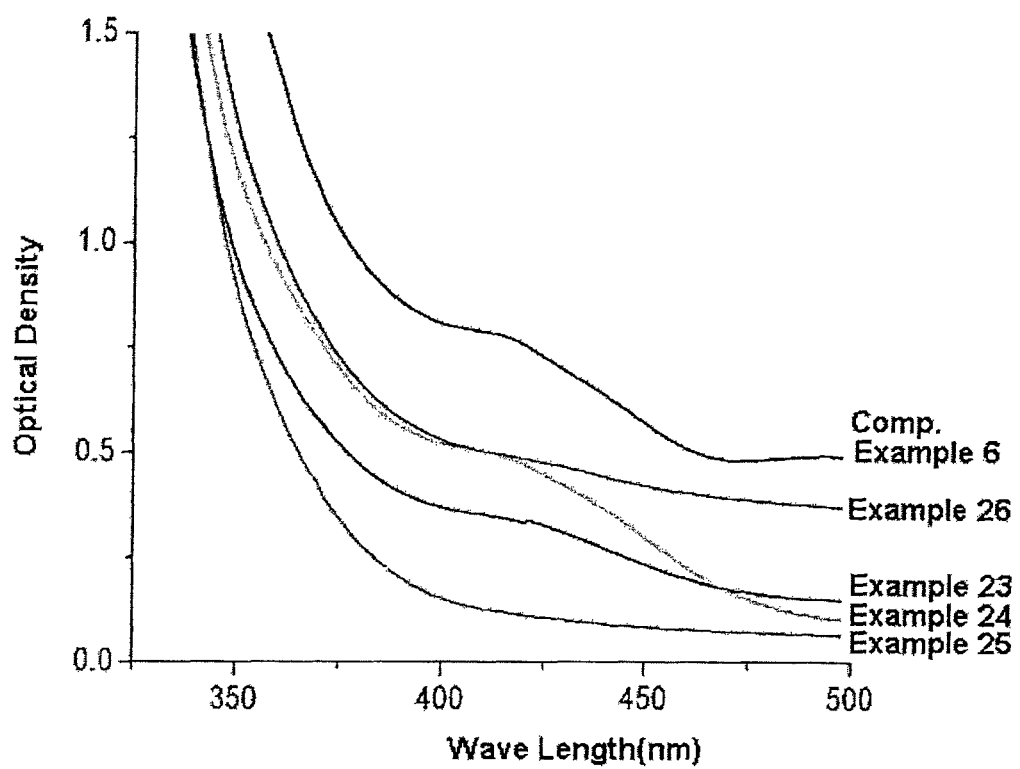
FIG. 4: optical densities of the copolymers obtained in Examples 23 to 26 and Comparative Example 6.

For the comparison, 20 g of propylene oxide was added to the resulting viscous liquid, and the content of cobalt in the copolymer solution was determined with an ICP-mass spectroscopy (Table 2: Comparative example 6). Further, after the solvent was removed from the solution, the residue (copolymer) was dissolved in 20 ml of methylene chloride, and determined optical density thereof with UV-Visible Spectrometer (FIG. 4). Propylene oxide was removed from the solution under a vacuum to obtain 4.1 g of the copolymer solution containing the polycarbonate and the complex was obtained (TON=13,000 and TOF=26,000).

Step 2

21 mg of a high molecular weight polyacrylate (PPA: Mv=3,000,000, 0.5% cross-linked, Aldrich) was added to the copolymer solution, and stirred at the room temperature for 2 hours. The resulting solution was filtered through cellite. The content of cobalt in the filtered solution was determined by using an ICP-mass spectroscopy (Table 2). After the solvent was removed from the copolymer solution, the copolymer was dissolved in 20 ml of methylene chloride, and its optical density was determined with UV-Visible Spectrometer (FIG. 4).

Example 24

The procedure of Example 23 was repeated except that a low molecular weight polyacrylate (Mv=450,000, 0.5% cross-linked) was used instead of the high molecular weight polyacylate. The content of cobalt in the filtered solution was determined by using an ICP-mass spectroscopy (Table 2). After the solvent was removed from the copolymer solution, the copolymer was dissolved in 20 ml of methylene chloride, and its optical density was determined with UV-Visible Spectrometer (FIG. 4).

Example 25

The resulting solution of the step 1 of Example 23 was filtered through a glass filter filled with silica gel (400 mg, particle size 0.040-0.063 mm, 230-400 mesh, Merck). The content of cobalt in the filtered solution was determined by using an ICP-mass spectroscopy (Table 2). After the solvent was removed from the copolymer solution, the copolymer was dissolved in 20 ml of methylene chloride, and its optical density was determined with UV-Visible Spectrometer (FIG. 4).

Example 26

The procedure of Example 25 was repeated except that the glass filter was filled with alumina (1.0 g, neutral, about 150 mesh, Sigma-Aldrich). The content of cobalt in the filtered solution was determined by using an ICP-mass spectroscopy (Table 2). After the solvent was removed from the copolymer solution, the copolymer was dissolved in 20 ml of methylene chloride, and its optical density was determined with UV-Visible Spectrometer (FIG. 4).

TABLE 2

| Example No. | Cobalt content (ppm) |
|---|---|
| Comparative Example 6 | 38 |
| Example 23 | 9.2 |
| Example 24 | 13 |
| Example 25 | 1.2 |
| Example 26 | 3.6 |

Example 27

The solid compound collected from the filtration of Example 23 was dispersed in methylene chloride solvent, 14 mg of 2,4-dinitrophenol was added thereto, and the solution turned red. The red solution was filtered and the solvent was removed under a vacuum. The residue was treated with diethyl ether to recover 5 mg of the inventive catalytic complex as a solid. The recovered catalysts showed same $^1$H-NMR spectrum and the same activity that observed for fresh virgin catalyst.

Example 28

The procedure of Example 27 was repeated with the solid compound collected from Example 24, and 6 mg of the inventive catalytic complex was recovered. The recovered catalysts showed same $^1$H-NMR spectrum and the same activity that observed for fresh virgin catalyst.

Examples 29 and 30

The procedure of Example 27 was repeated except that the solid compounds collected from Examples 25 and 26 were dispersed in methanol solvent, respectively. According to $^1$H-NMR analyses, the recovered catalysts comprise additional 2 moles of 2,4-dinitrophenolate per mole of cobalt, which showed about ⅔ of the initial activity.

Examples 31 and 32

Solid compounds collected from the filtration of Examples 25 and 26 were respectively dispersed into methanol saturated with $NaBF_4$, and the solution turned red. The red solution was filtered, and the filtrate was washed with methanol saturated with $NaBF_4$ until the solution became colorless.

The solvent was removed under a vacuum, and the residue was dissolved in methylene chloride. An excessive amount of solid sodium 2,4-dinitrophenolate (4 equivalents based on added catalyst) and 2,4-dinitrophenol (2 equivalent) were added to the methylene chloride solution and stirred overnight. The solution was filtered over Celite, and the solvent was removed from the filtered solution to obtain the catalyst as a brown powder. The recovered catalysts showed same $^1$H-NMR spectrum and the same activity that observed for fresh virgin catalyst.

Example 33

The procedure of Example 23 was repeated except that 95 mg of the Compound 44 prepared in Example 5 and propylene oxide (250.0 g) were place in a 500 mL bomb reactor. The reaction was allowed to proceed for 1 hour and 5 minutes.

250 g of propylene oxide was added to the resulting viscous liquid. The resulting solution was filtered through a silica gel column (12 g, 230-400 mesh, Merck). The solvent was recycled by a vacuum transfer and 92 g of copolymer was obtained (TON is 21,000 and TOF is 19,000 h$^{-1}$)

The red solid collected on the surface layer of the silica was dissolved in methanol saturated with NaBF$_4$, the resulting solution was filtered and washed with methanol saturated with NaBF$_4$ until the solution became colorless. The solvent was removed under a vacuum, and the residue was dissolved into methylene chloride. An excessive amount of solid sodium 2,4-dinitrophenolate (4 equivalents based on added catalyst) and 2,4-dinitrophenol (2 equivalent) were added to the resulting solution and stirred overnight. The solvent was removed to obtain the catalyst as a brown powder (82 mg, recovery yield=86%). The recovered catalysts showed same $^1$H-NMR spectrum and it could be used for subsequent batch without significant loss of activity. Table 2 shows the polymerization results using the recovered catalyst. In the repeated polymerizations, some reductions of the selectivity from >99% to 97-98% and the molecular weights from about 300,000 to about 200,000 was observed. The recovery yields were 85-89%; some of this loss is attributed to the necessarily incomplete transfer of the polymerization solution from the reactor to the filtration apparatus. The lost catalyst was supplemented with a fresh material for each subsequent batch.

TABLE 3

90-g scale CO$_2$/(propylene oxide) copolymerization using the recovered catalyst of Compound 44.

| Run # | Time (h) | Yield (g) | TON | Selectivity | Mn × 10$^{-3}$ | Mw/Mn |
|---|---|---|---|---|---|---|
| 1st | 65 | 92 | 21000 | >99 | 296 | 1.19 |
| 2nd | 85 | 90 | 21000 | 98 | 172 | 1.41 |
| 3rd | 85 | 89 | 21000 | 97 | 176 | 1.34 |
| 4th | 80 | 88 | 21000 | 98 | 190 | 1.22 |
| 5th | 90 | 85 | 20000 | 97 | 210 | 1.21 |

While the invention has been described with respect to the specific embodiments, it should be recognized that various modifications and changes may be made by those skilled in the art to the invention which also fall within the scope of the invention as defined by the appended claims.

What is claimed is:

1. A compound of formula (7a):

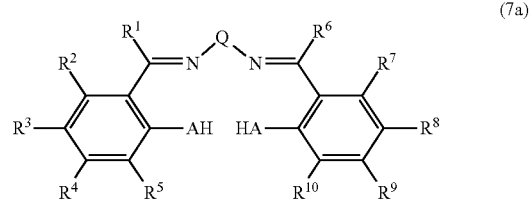

(7a)

wherein

A is oxygen;

Q is trans-1,2-cyclohexylene, ethylene or substituted ethylene;

R$^1$, R$^2$, R$^4$, R$^6$, R$^7$ and R$^9$ are hydrogen;

R$^5$ and R$^{10}$ are each independently hydrogen, tert-butyl, methyl or isopropyl;

one or both of R$^3$ and R$^8$ are —[YR$^{41}_{3-m}${(CR$^{42}$R$^{43}$)$_n$NR$^{44}$R$^{45}$R$^{46}$}$_m$]X'$_m$ or —[PR$^{51}$R$^{52}$=N=PR$^{53}$R$^{54}$R$^{55}$] X', and the other is hydrogen, methyl, isopropyl or tert-butyl;

X' is each independently halogen; C$_6$-C$_{20}$ aryloxy unsubstituted or substituted by nitro; or C$_1$-C$_{20}$ carboxy unsubstituted or substituted by halogen;

Y is C or Si;

R$^{41}$, R$^{42}$, R$^{43}$, R$^{44}$, R$^{45}$, R$^{46}$, R$^{51}$, R$^{52}$, R$^{53}$, R$^{54}$ and R$^{55}$ are each independently hydrogen; C$_1$-C$_{20}$ alkyl; C$_1$-C$_{20}$ alkyl having one or more functional moieties selected from the group consisting of halogen, nitrogen, oxygen, silicon, sulfur and phosphorous; C$_2$-C$_{20}$ alkenyl; C$_2$-C$_{20}$ alkenyl having one or more functional moieties selected from the group consisting of halogen, nitrogen, oxygen, silicon, sulfur and phosphorous; C$_7$-C$_{20}$ alkylaryl; C$_7$-C$_{20}$ alkylaryl having one or more functional moieties selected from the group consisting of halogen, nitrogen, oxygen, silicon, sulfur and phosphorous; C$_7$-C$_{20}$ arylalkyl; C$_7$-C$_{20}$ arylalkyl having one or more functional moieties selected from the group consisting of halogen, nitrogen, oxygen, silicon, sulfur and phosphorous; or a metalloid radical of group XIV metal substituted by hydrocarbyl, two of R$^{44}$, R$^{45}$ and R$^{46}$, or two of R$^{51}$, R$^{52}$, R$^{53}$, R$^{54}$ and R$^{55}$ being optionally fused together to form a bridged structure;

m is an integer in the range of 1 to 3; and n is an integer in the range of 1 to 20.

2. The compound of claim 1, which is represented by any one of formulae (8a) to (8e):

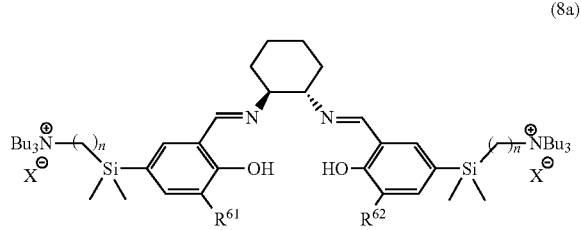

(8a)

(8b)
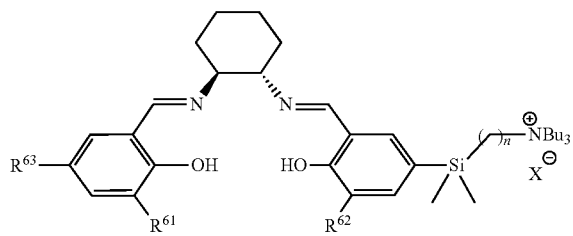

(8e)
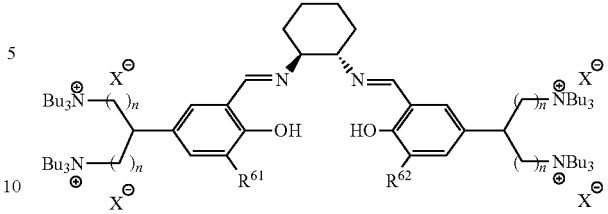

(8c)
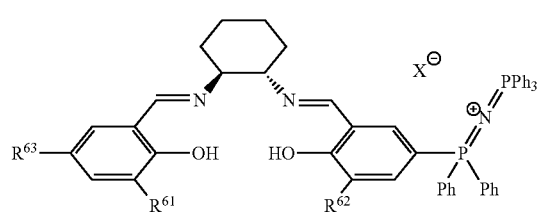

wherein
$R^{61}$, $R^{62}$ and $R^{63}$ are each independently hydrogen, methyl, isopropyl or tert-butyl;

X is halogen; $BF_4$; $C_6$-$C_{20}$ aryloxy; $C_6$-$C_{20}$ aryloxy having one or more functional moieties selected from the group consisting of halogen, nitrogen, oxygen, silicon, sulfur and phosphorous; $C_1$-$C_{20}$ carboxy; $C_1$-$C_{20}$ carboxy having one or more functional moieties selected from the group consisting of halogen, nitrogen, oxygen, silicon, sulfur and phosphorous; $C_1$-$C_{20}$ alkoxy; $C_1$-$C_{20}$ alkoxy having one or more functional moieties selected from the group consisting of halogen, nitrogen, oxygen, silicon, sulfur and phosphorous; $C_1$-$C_{20}$ alkylsulfonato; $C_1$-$C_{20}$ alkylsulfonato having one or more functional moieties selected from the group consisting of halogen, nitrogen, oxygen, silicon, sulfur and phosphorous; $C_1$-$C_{20}$ amido; or $C_1$-$C_{20}$ amido having one or more functional moieties selected from the group consisting of halogen, nitrogen, oxygen, silicon, sulfur and phosphorous; and n is an integer in the range of 1 to 20.

3. The compound of claim 2, which is represented by any one of formulae (9a) to (9e):

(8d)
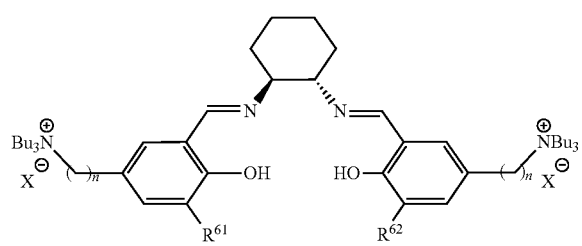

(9a)
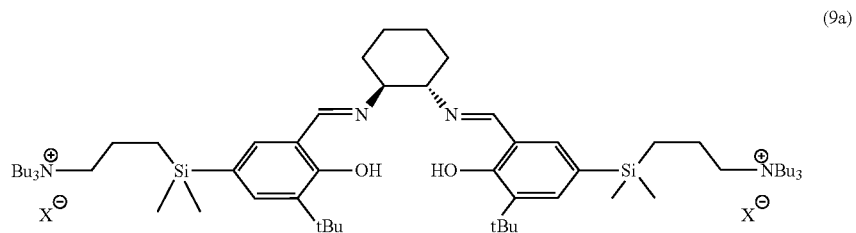

wherein X is halogen, $BF_4$ or 2,4-dinitrophenoxy;

(9b)
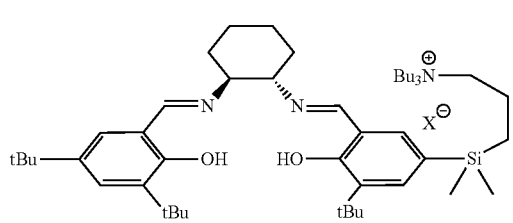

wherein X is halogen, BF₄ or 2,4-dinitrophenoxy;
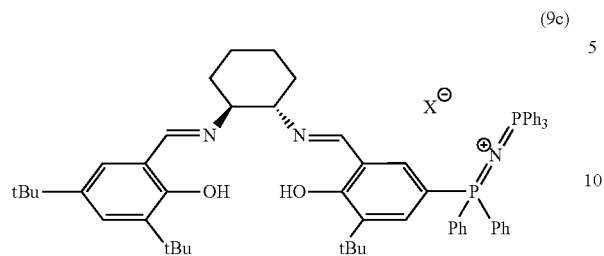
(9c)
wherein X is halogen, BF₄ or 2,4-dinitrophenoxy;
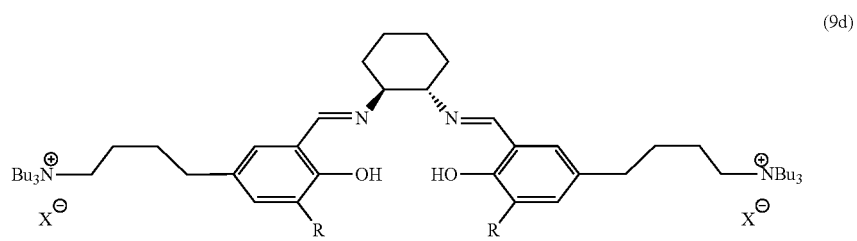
(9d)
wherein X is halogen, BF₄ or 2,4-dinitrophenoxy, and R is methyl, isopropyl or tert-butyl; and
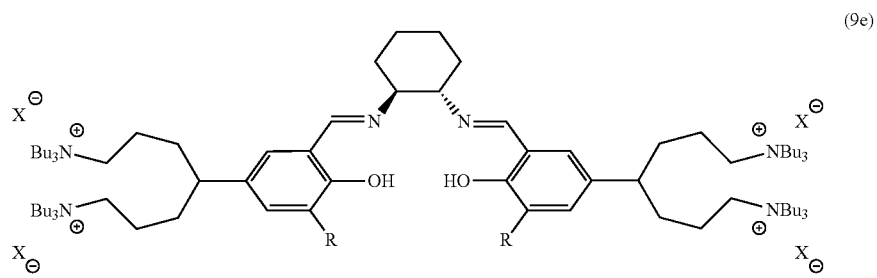
(9e)
wherein X is halogen, BF₄ or 2,4-dinitrophenoxy, and R is methyl, isopropyl or tert-butyl.
* * * * *